United States Patent
Pilla

(10) Patent No.: US 10,207,122 B2
(45) Date of Patent: Feb. 19, 2019

(54) METHOD AND APPARATUS FOR ELECTROMAGNETIC ENHANCEMENT OF BIOCHEMICAL SIGNALING PATHWAYS FOR THERAPEUTICS AND PROPHYLAXIS IN PLANTS, ANIMALS AND HUMANS

(71) Applicant: Endonovo Therapeutics, Inc., Woodlands Hills, CA (US)

(72) Inventor: Arthur A. Pilla, Oakland, NJ (US)

(73) Assignee: Endonovo Therapeutics, Inc., Woodland Hills, CA (US)

( * ) Notice: Subject to any disclaimer, the term of this patent is extended or adjusted under 35 U.S.C. 154(b) by 725 days.

(21) Appl. No.: 14/687,716

(22) Filed: Apr. 15, 2015

(65) Prior Publication Data
US 2015/0217126 A1    Aug. 6, 2015

Related U.S. Application Data

(60) Division of application No. 13/285,761, filed on Oct. 31, 2011, now Pat. No. 9,656,096, which is a
(Continued)

(51) Int. Cl.
*A61N 1/40* (2006.01)
*A61N 2/02* (2006.01)
(Continued)

(52) U.S. Cl.
CPC .............. *A61N 2/02* (2013.01); *A01G 7/04* (2013.01); *A61N 1/40* (2013.01); *A61N 2/008* (2013.01)

(58) Field of Classification Search
CPC . A61N 2/02; A61N 2/00; A61N 2/004; A61N 2/006; A61N 2/008
(Continued)

(56) References Cited

U.S. PATENT DOCUMENTS

| 1,233,841 A | 7/1917 | Butcher |
| 2,130,758 A | 9/1938 | Rose |

(Continued)

FOREIGN PATENT DOCUMENTS

| CA | 0608693 | 11/1960 |
| CN | 1052053 A | 6/1991 |

(Continued)

OTHER PUBLICATIONS

Pilla et al.; U.S. Appl. No. 14/171,613 entitled "Apparatus and method for electromagnetic treatment of neurodegenerative conditions," filed Feb. 3, 2014.
(Continued)

*Primary Examiner* — Samuel Gilbert
(74) *Attorney, Agent, or Firm* — Roland Tong

(57) ABSTRACT

Apparatus and methods for delivering electromagnetic signals configured specifically to accelerate the asymmetrical kinetics of the binding of intracellular ions to their respective intracellular buffers, to enhance the biochemical signaling pathways plant animal and human molecules, cells, tissues, organs, portions of entire organisms and entire organisms employ for growth, repair and maintenance. Described herein are devices and methods that utilize repetitive bursts of waveforms configured to maximize the bound concentration of intracellular ions at their associated molecular buffers to enhance the biochemical signaling pathways living systems employ for growth, repair and maintenance. For example the systems and methods described herein may drive the binding of calcium to calmodulin (CaM), thereby enhancing the CaM-dependent nitric oxide (NO)/cyclic guanosine monophosphate (cGMP) signaling pathway.

22 Claims, 11 Drawing Sheets

Related U.S. Application Data continuation-in-part of application No. 12/819,956, filed on Jun. 21, 2010, now abandoned, which is a continuation-in-part of application No. 12/772,002, filed on Apr. 30, 2010, now abandoned, which is a continuation of application No. 11/003,108, filed on Dec. 3, 2004, now Pat. No. 7,744,524, said application No. 12/819,956 is a continuation-in-part of application No. 11/114,666, filed on Apr. 26, 2005, now Pat. No. 7,740,574, and a continuation-in-part of application No. 11/110,000, filed on Apr. 19, 2005, now abandoned, said application No. 12/819,956 is a continuation-in-part of application No. 11/369,308, filed on Mar. 6, 2006, now abandoned, and a continuation-in-part of application No. 11/369,309, filed on Mar. 6, 2006, now abandoned, said application No. 12/819,956 is a continuation-in-part of application No. 11/223,073, filed on Sep. 10, 2005, now Pat. No. 7,758,490, and a continuation-in-part of application No. 11/339,204, filed on Jan. 25, 2006, now abandoned, and a continuation-in-part of application No. 11/818,065, filed on Jun. 12, 2007, now abandoned, and a continuation-in-part of application No. 11/903,294, filed on Sep. 20, 2007, now abandoned, and a continuation-in-part of application No. 11/977,043, filed on Oct. 22, 2007, now abandoned.

(60) Provisional application No. 61/456,036, filed on Oct. 29, 2010, provisional application No. 60/527,327, filed on Dec. 5, 2003, provisional application No. 60/564,887, filed on Apr. 26, 2004, provisional application No. 60/563,104, filed on Apr. 19, 2004, provisional application No. 60/568,967, filed on Mar. 7, 2005, provisional application No. 60/568,968, filed on Mar. 7, 2005, provisional application No. 60/812,841, filed on Jun. 12, 2006, provisional application No. 60/846,126, filed on Sep. 20, 2006, provisional application No. 60/852,927, filed on Oct. 20, 2006.

(51) Int. Cl.
*A01G 7/04* (2006.01)
*A61N 2/00* (2006.01)

(58) Field of Classification Search
USPC ........................................ 600/9–15
See application file for complete search history.

(56) References Cited

U.S. PATENT DOCUMENTS

| | | |
|---|---|---|
| 2,276,996 A | 3/1942 | Milinowski |
| 2,648,727 A | 8/1953 | Rockwell |
| 3,043,310 A | 7/1962 | Milinowski |
| 3,181,535 A | 5/1965 | Milinowski |
| 3,270,746 A | 9/1966 | Kendall et al. |
| 3,329,148 A | 7/1967 | Kendall |
| 3,329,149 A | 7/1967 | Kendall et al. |
| 3,800,802 A | 4/1974 | Berry et al. |
| 3,890,953 A | 6/1975 | Kraus et al. |
| 3,915,151 A | 10/1975 | Kraus |
| 3,952,751 A | 4/1976 | Yarger |
| 3,978,864 A | 9/1976 | Smith |
| 4,028,518 A | 6/1977 | Boudouris et al. |
| 4,105,017 A | 8/1978 | Ryaby et al. |
| 4,197,851 A | 4/1980 | Fellus |
| 4,266,532 A | 5/1981 | Ryaby et al. |
| 4,305,115 A | 12/1981 | Armitage |
| 4,315,503 A | 2/1982 | Ryaby et al. |
| 4,338,945 A | 7/1982 | Kosugi et al. |
| 4,340,063 A | 7/1982 | Maurer |
| 4,374,482 A | 2/1983 | Moore et al. |
| 4,428,366 A | 1/1984 | Findl et al. |
| 4,454,882 A | 6/1984 | Takano |
| 4,548,208 A | 10/1985 | Niemi |
| 4,550,714 A | 11/1985 | Talish et al. |
| 4,556,051 A | 12/1985 | Maurer |
| 4,616,629 A | 10/1986 | Moore |
| 4,627,438 A | 12/1986 | Liss et al. |
| 4,654,574 A | 3/1987 | Thaler |
| 4,672,951 A | 6/1987 | Welch |
| 4,674,482 A | 6/1987 | Waltonen et al. |
| 4,765,310 A | 8/1988 | Deagle |
| 4,793,325 A | 12/1988 | Cadossi et al. |
| 4,829,984 A | 5/1989 | Gordon |
| 4,850,372 A | 7/1989 | Ko et al. |
| 4,889,526 A | 12/1989 | Rauscher et al. |
| 4,926,881 A | 5/1990 | Ichinomiya et al. |
| 4,940,453 A | 7/1990 | Cadwell |
| 4,993,413 A | 2/1991 | McLeod et al. |
| 4,998,532 A | 3/1991 | Griffith |
| 5,000,178 A | 3/1991 | Griffith |
| 5,014,699 A | 5/1991 | Pollack et al. |
| 5,116,304 A | 5/1992 | Cadwell |
| 5,123,898 A | 6/1992 | Liboff et al. |
| 5,147,284 A | 9/1992 | Federov et al. |
| 5,181,902 A | 1/1993 | Erickson et al. |
| 5,224,922 A | 7/1993 | Kurtz |
| 5,314,401 A | 5/1994 | Tepper |
| 5,338,286 A | 8/1994 | Abbott et al. |
| 5,370,680 A | 12/1994 | Proctor |
| 5,386,837 A | 2/1995 | Sterzer |
| 5,407,421 A | 4/1995 | Goldsmith |
| 5,441,495 A | 8/1995 | Liboff et al. |
| 5,478,303 A | 12/1995 | Foley-Nolan et al. |
| 5,480,373 A | 1/1996 | Fischer et al. |
| 5,518,496 A | 5/1996 | McLeod et al. |
| 5,529,569 A | 6/1996 | Woo |
| 5,584,863 A | 12/1996 | Rauch et al. |
| 5,595,564 A | 1/1997 | Pinna |
| 5,707,334 A | 1/1998 | Young |
| 5,718,246 A | 2/1998 | Vona |
| 5,718,721 A | 2/1998 | Ross |
| 5,723,001 A | 3/1998 | Pilla et al. |
| 5,743,844 A | 4/1998 | Tepper et al. |
| 5,778,894 A | 7/1998 | Dorogi et al. |
| 5,792,209 A | 8/1998 | Varner et al. |
| 5,814,078 A | 9/1998 | Zhou et al. |
| 5,877,627 A | 3/1999 | Fischer et al. |
| 5,908,444 A | 6/1999 | Azure |
| 5,951,459 A | 9/1999 | Blackwell |
| 5,968,527 A | 10/1999 | Litovitz |
| 5,990,177 A | 11/1999 | Brown |
| 5,997,464 A | 12/1999 | Blackwell |
| 6,004,257 A | 12/1999 | Jacobson |
| 6,083,149 A | 7/2000 | Wascher et al. |
| 6,086,525 A | 7/2000 | Davey et al. |
| 6,099,459 A | 8/2000 | Jacobson |
| 6,132,362 A | 10/2000 | Tepper et al. |
| 6,149,577 A | 11/2000 | Bouldin et al. |
| 6,155,966 A | 12/2000 | Parker |
| 6,190,893 B1 | 2/2001 | Shastri et al. |
| 6,200,259 B1 | 3/2001 | March |
| 6,213,934 B1 | 4/2001 | Bianco et al. |
| 6,231,187 B1 | 5/2001 | Munoz et al. |
| 6,231,528 B1 | 5/2001 | Kaufman et al. |
| 6,234,953 B1 | 5/2001 | Thomas et al. |
| 6,246,912 B1 | 6/2001 | Sluijter et al. |
| 6,261,221 B1 | 7/2001 | Tepper et al. |
| 6,261,831 B1 | 7/2001 | Agee |
| 6,301,506 B1 | 10/2001 | den Boer et al. |
| 6,321,120 B1 | 11/2001 | Surbeck et al. |
| 6,334,069 B1 | 12/2001 | George et al. |
| 6,348,070 B1 | 2/2002 | Teissl et al. |
| 6,418,345 B1 | 7/2002 | Tepper et al. |
| 6,421,562 B1 | 7/2002 | Ross |
| 6,424,863 B1 | 7/2002 | Flock et al. |
| 6,434,426 B1 | 8/2002 | Munneke et al. |

(56) References Cited

U.S. PATENT DOCUMENTS

| | | |
|---|---|---|
| 6,443,883 B1 | 9/2002 | Ostrow et al. |
| 6,450,941 B1 | 9/2002 | Larson |
| 6,458,151 B1 | 10/2002 | Saltiel |
| 6,458,157 B1 | 10/2002 | Suaning et al. |
| 6,463,336 B1 | 10/2002 | Mawhinney |
| 6,556,872 B2 | 4/2003 | Hauck |
| 6,560,489 B2 | 5/2003 | Hauck |
| 6,561,968 B1 | 5/2003 | Dissing et al. |
| 6,569,654 B2 | 5/2003 | Shastri et al. |
| 6,589,159 B2 | 7/2003 | Paturu |
| 6,629,971 B2 | 10/2003 | McDaniel |
| 6,648,812 B2 | 11/2003 | Ardizzone |
| 6,675,047 B1 | 1/2004 | Konoplev et al. |
| 6,678,562 B1 | 1/2004 | Tepper et al. |
| 6,684,108 B2 | 1/2004 | Surbeck et al. |
| 6,701,185 B2 | 3/2004 | Burnett et al. |
| 6,839,589 B2 | 1/2005 | Petlan |
| 6,844,378 B1 | 1/2005 | Martin et al. |
| 6,919,205 B2 | 7/2005 | Brighton |
| 6,934,580 B1 | 8/2005 | Osorio et al. |
| 6,955,642 B1 | 10/2005 | Simon |
| 7,010,353 B2 | 3/2006 | Gan et al. |
| 7,022,506 B2 | 4/2006 | Brighton et al. |
| 7,089,060 B1 | 8/2006 | Fitzsimmons |
| 7,130,692 B2 | 10/2006 | Brighton et al. |
| 7,160,241 B1 | 1/2007 | Herbst |
| 7,175,587 B2 | 2/2007 | Gordon et al. |
| 7,177,695 B2 | 2/2007 | Moran |
| 7,177,696 B1 | 2/2007 | Pandelisev |
| 7,215,995 B2 | 5/2007 | Brighton et al. |
| 7,288,062 B2 | 10/2007 | Spiegel |
| 7,333,858 B2 | 2/2008 | Killian et al. |
| 7,419,474 B2 | 9/2008 | Lee |
| 7,429,471 B2 | 9/2008 | Brighton |
| 7,456,189 B2 | 11/2008 | Himmelsbach et al. |
| 7,465,546 B2 | 12/2008 | Brighton |
| 7,465,566 B2 | 12/2008 | Brighton et al. |
| 7,520,849 B1 | 4/2009 | Simon |
| 7,566,295 B2 | 7/2009 | Giardino et al. |
| 7,740,574 B2 | 6/2010 | Pilla et al. |
| 7,744,524 B2 | 6/2010 | Pilla |
| 7,758,490 B2 | 7/2010 | Pilla et al. |
| 7,896,797 B2 | 3/2011 | Pilla et al. |
| 8,167,784 B1 | 5/2012 | Honeycutt et al. |
| 8,343,027 B1 | 1/2013 | DiMino et al. |
| 8,415,123 B2 | 4/2013 | Pilla et al. |
| 8,961,385 B2 | 2/2015 | Pilla et al. |
| 2001/0007937 A1 | 7/2001 | MacKin |
| 2001/0031906 A1 | 10/2001 | Ishikawa et al. |
| 2001/0041820 A1 | 11/2001 | Woo |
| 2001/0044643 A1 | 11/2001 | Litovitz |
| 2002/0035358 A1 | 3/2002 | Wang |
| 2003/0023283 A1 | 1/2003 | McDaniel |
| 2003/0028072 A1 | 2/2003 | Fischell et al. |
| 2003/0093028 A1 | 5/2003 | Spiegel |
| 2003/0099979 A1 | 5/2003 | Ohtani et al. |
| 2003/0125769 A1 | 7/2003 | Brighton |
| 2003/0171640 A1 | 9/2003 | Canedo |
| 2004/0176803 A1 | 9/2004 | Whelan et al. |
| 2004/0176805 A1 | 9/2004 | Whelan et al. |
| 2004/0176806 A1 | 9/2004 | Markoll |
| 2004/0267333 A1 | 12/2004 | Kronberg |
| 2005/0049640 A1 | 3/2005 | Gurtner et al. |
| 2005/0059153 A1 | 3/2005 | George et al. |
| 2005/0182287 A1 | 8/2005 | Becker |
| 2005/0215842 A1 | 9/2005 | Pilla et al. |
| 2005/0222625 A1 | 10/2005 | Laniado et al. |
| 2005/0251229 A1 | 11/2005 | Pilla et al. |
| 2006/0009825 A1 | 1/2006 | Chiriaev et al. |
| 2006/0161226 A1 | 7/2006 | McMickle |
| 2006/0206174 A1 | 9/2006 | Honeycutt et al. |
| 2006/0212077 A1 | 9/2006 | Pilla et al. |
| 2006/0293724 A1 | 12/2006 | Kronberg et al. |
| 2007/0026514 A1 | 2/2007 | Pilla et al. |
| 2007/0043254 A1 | 2/2007 | DeMarco |
| 2007/0060954 A1 | 3/2007 | Cameron et al. |
| 2007/0149901 A1 | 6/2007 | Gordon et al. |
| 2007/0173904 A1 | 7/2007 | Pilla |
| 2007/0203390 A1 | 8/2007 | Rohan et al. |
| 2007/0282156 A1 | 12/2007 | Konings |
| 2007/0288072 A1 | 12/2007 | Pascual-Leone et al. |
| 2007/0299472 A1 | 12/2007 | Brighton |
| 2008/0039901 A1 | 2/2008 | Kronberg et al. |
| 2008/0058793 A1 | 3/2008 | Pilla et al. |
| 2008/0132971 A1 | 6/2008 | Pilla et al. |
| 2008/0140155 A1 | 6/2008 | Pilla et al. |
| 2008/0200749 A1 | 8/2008 | Zheng et al. |
| 2008/0208287 A1 | 8/2008 | Palermo et al. |
| 2008/0217263 A1 | 9/2008 | Higgins et al. |
| 2008/0288035 A1 | 11/2008 | Gill et al. |
| 2009/0018613 A1 | 1/2009 | Brighton |
| 2009/0030476 A1 | 1/2009 | Hargrove |
| 2009/0043188 A1 | 2/2009 | Rauscher |
| 2009/0099623 A1 | 4/2009 | Bentwich |
| 2009/0105781 A1 | 4/2009 | Brighton |
| 2009/0216068 A1 | 8/2009 | Thomas et al. |
| 2009/0326315 A1 | 12/2009 | Nishi et al. |
| 2010/0004500 A1 | 1/2010 | Gliner et al. |
| 2010/0005571 A1 | 1/2010 | Moss et al. |
| 2010/0121407 A1 | 5/2010 | Pfaff et al. |
| 2010/0210893 A1 | 8/2010 | Pilla |
| 2010/0222631 A1 | 9/2010 | Pilla |
| 2010/0331603 A1* | 12/2010 | Szecsi ............... A61N 2/006 600/13 |
| 2011/0112352 A1 | 5/2011 | Pilla et al. |
| 2011/0152598 A1 | 6/2011 | Pilla et al. |
| 2011/0184223 A1 | 7/2011 | Peterchev et al. |
| 2011/0190849 A1 | 8/2011 | Faltys et al. |
| 2011/0213195 A1 | 9/2011 | Kraus et al. |
| 2012/0089201 A1 | 4/2012 | Pilla |
| 2012/0116149 A1 | 5/2012 | Pilla et al. |
| 2013/0035539 A1 | 2/2013 | Kornstein |
| 2013/0274540 A1 | 10/2013 | Pilla et al. |
| 2014/0046115 A1 | 2/2014 | Pilla |
| 2014/0046117 A1 | 2/2014 | Pilla |
| 2014/0213843 A1 | 7/2014 | Pilla et al. |
| 2014/0213844 A1 | 7/2014 | Pilla et al. |
| 2014/0303425 A1 | 10/2014 | Pilla et al. |

FOREIGN PATENT DOCUMENTS

| | | |
|---|---|---|
| CN | 1408448 A | 4/2003 |
| CN | 102006793 A | 4/2011 |
| CN | 102151362 A | 8/2011 |
| DE | 970276 | 9/1958 |
| EP | 543152 A2 | 10/1992 |
| EP | 0500983 | 7/1995 |
| EP | 1167070 A1 | 1/2002 |
| FR | 748828 | 4/1933 |
| GB | 0604107 | 6/1948 |
| GB | 2162066 | 1/1986 |
| GB | 2400316 A | 10/2004 |
| JP | 03-523271 | 8/2003 |
| WO | WO 83/01742 A1 | 5/1983 |
| WO | WO 95/27533 | 10/1995 |
| WO | WO 96/11723 | 4/1996 |
| WO | WO 2004/108208 A2 | 12/2004 |
| WO | WO 2005/051306 A2 | 6/2005 |
| WO | WO 2008/070001 A2 | 6/2008 |
| WO | WO 2009/155516 | 12/2009 |
| WO | WO 2010/067336 A2 | 6/2010 |
| WO | WO 2011/053607 A1 | 5/2011 |

OTHER PUBLICATIONS

Pilla et al.; U.S. Appl. No. 14/608,140 entitled "Devices and method for treatment of degenerative joint diseases with electromagnetic fields," filed Jan. 28, 2015.

Dimino et al.; U.S. Appl. No. 14/688,602 entitled "Two-part pulsed electromagnetic field applicator for application of therapeutic energy," filed Apr. 16, 2015.

(56) References Cited

OTHER PUBLICATIONS

Aaron et al.; Power frequency fields promote cell differentiation coincident with an increase in transforming growth factor-?1 expression; Bioelectromagnetic; vol. 20 (7); pp. 453-458; Oct. 1999.

Aaron et al.; The conservative treatment of osteonecrosis of the femoral head. A comparison of core decompression and pulsing electromagnetic fields; Clin. Orthopaed. Rel. Res.; vol. 249; pp. 209-218; Dec. 1989.

Adair; A physical analysis of the ion parametric resonance model; Bioelectromagnetics; vol. 19(3); pp. 181-191; Dec. 1998.

Adair; Comment: Analyses of Models of Ion Actions Under the Combined Action of AC and DC Magnetic Fields; Bioelectromagnetics; vol. 27; No. 4; pp. 332-334; May 2006.

Adair; Criticism of Lednev's mechanism for the influence of weak magnetic fields on biological systems; Bioelectromagnetics; vol. 13 (3); pp. 231-235; Feb. 1992.

Adair; Static and low-frequency magnetic field effects: Health risks and therapies; Rep Prog Phys; vol. 63 (3); pp. 415-454; Mar. 2000.

Akai et al.; Effect of electrical stimulation on musculoskeletal systems: a meta-analysis of controlled clinical trials; Bioelectromagnetics; vol. 23 (2); pp. 132-143; Feb. 2002.

Albensi et al.; Diffusion and high resolution MRI of traumatic brain injury in rats: time course and correlation with histology. Exp Neurol 162, 61-72 (Mar. 2000).

Anderson et al.; Fluoro-jade B stains quiescent and reactive astrocytes in the rodent spinal cord. J Neurotrauma 20, 1223-31 (Nov. 2003).

Arendash et al.; Electromagnetic Field Treatment Protects Against and Reverses Cognitive Impairment in Alzheimer's Disease Mice. Journal of Alzheimer's Disease vol. 19, 191-210 (Jan. 2010).

Armonda et al.; Wartime traumatic cerebral vasospasm: recent review of combat casualties. Neurosurgery 59, 1215-25; discussion 1225 (Dec. 2006).

Arnold et al.; Nitric oxide activates guanylate cyclase and increases guanosine 3':5'-cyclic monophosphate levels in various tissue preparations. Proc Natl Acad Sci U S A 74, 3203-7 (Aug. 1977).

Auffray et al.; Blood monocytes: development, heterogeneity, and relationship with dendritic cells. Annu Rev Immunol 27, 669-92 (Jan. 2009).

Ayrapetyan et al.; Magnetic fields alter electrical properties of solutions and their physiological effects; Bioelectromagnetics; vol. 15 (2); pp. 133-142; (year of pub. sufficiently earlier than effective US filing date and any foreign priority date) 1994.

Barger et al.; Microglial Activation by Alzheimer Amyloid Precursor Protein and Modulation by Apolipoprotein E. Nature; vol. 388; 878-881 (Aug. 1997).

Bassett et al.; A non-operative salvage of surgically-resistant pseudoarthroses and non-unions by pulsing electromagnetic fields; Clin Orthop; vol. 124; pp. 117-131; May 1977.

Bassett et al.; Generation of electric potentials by bone in response to mechanical stress. Science 137, 1063-4 (Sep. 28, 1962).

Bassett, C. A.; Biological significance of piezoelectricity. Calc. Tiss. Res. 1, 252 (Dec. 1968).

Bawin et al.; Effects of modulated VHF fields on the central nervous system; Ann NY Acad Sci; vol. 247; pp. 74-81; Feb. 1975.

Bawin et al.; Sensitivity of calcium binding in cerebral tissue to weak environmental electric fields oscillating at low frequency; Proc Nat''l Acad Sci, USA; 73(6); pp. 1999-2003; Jun. 1976.

Bearden Jr.; Quantitation of submicrogram quantities of protein by an improved protein-dye binding assay; Biochim Biophys Acta; vol. 533(2); pp. 525-529; Apr. 26, 1978.

Beaumont et al.; The effects of human corticotrophin releasing factor on motor and cognitive deficits after impact acceleration injury. Neurol Res 22, 665-73 (Oct. 2000).

Beaumont et al.; The impact-acceleration model of head injury: injury severity predicts motor and cognitive performance after trauma. Neurol Res 21, 742-54 (Dec. 1999).

Beck et al.; The Bioelectromagnetics Society (History of the first 25 years); eds. Shappard, A. and Blackman, C.; 46 pgs.; (year of publication is sufficiently earlier than the effective U.S. filing date and any foreign priority date) 2004.

Becker, T. O.; The bioelectric factors in amphibian limb regeneration. J. Bone Joint Surg. 43A, 643 (Jul. 1961).

Bederson et al.; Nuclear magnetic resonance imaging and spectroscopy in experimental brain edema in a rat model. J Neurosurg 64, 795-802 (May 1986).

Belanger et al.; Cognitive sequelae of blast-related versus other mechanisms of brain trauma. J Int Neuropsychol Soc 15(1), 1-8 (Jan. 2009).

Belyaev et al.; Frequency-dependent Effects of ELF Magnetic Field on Cromatin Conformation in *Escherichia coli* Cells and Human Lymphocytes; Biochimica et Biophysica Acta; vol. 1526(3); pp. 269-276; Jun. 15, 2001.

Binder et al.; Pulsed electromagnetic field therapy of persistent rotator cuff tendinitis: a double blind controlled assessment; Lancet; vol. 1 (8379); pp. 695-697; Mar. 31, 1984.

Blackman et al.; A role for the magnetic field in the radiation induced efflux of calcium ions from brain tissue in vitro; Bioelectromagnetics; vol. 6(4); pp. 327-337; (year of pub. sufficiently earlier than effective US filing date and any foreign priority date) 1985.

Blackman et al.; Action of 50 Hz magnetic fields on neurite outgrowth in pheochromocytoma cells. Bioelectromagnetics 14, 273-86 (year of publication is sufficiently earlier than the effective U.S. filing date and any foreign priority date) (1993).

Blackman et al.; Effects of ELF fields on calcium-ion efflux from brain tissue in vitro; Radiat Res; vol. 92(3); pp. 510-520; Dec. 1982.

Blackman et al.; Empirical test of an ion parametric resonance model for magnetic field interactions with PC-12 cells; Bioelectromagnetics; vol. 15(3): pp. 239-260; (year of pub. sufficiently earlier than effective US filing date and any foreign priority date) 1994.

Blackman et al.; Influence of electromagnetic fields on the efflux of calcium ions from brain tissue in vitro: A three-model analysis consistent with the frequency response up to 510 Hz; Bioelectromagnetics; vol. 9(3); pp. 215-227; (year of pub. sufficiently earlier than effective US filing date and any foreign priority date) 1988.

Blackman et al.; Multiple power-density windows and their possible origin; Bioelectromagnetics; vol. 10(2); pp. 115-128; (year of pub. sufficiently earlier than effective US filing date and any foreign priority date) 1989.

Blanchard et al.; Clarification and application of an ion parametric resonance model for magnetic field interactions with biological systems; Bioelectromagnetics; vol. 15(3); pp. 217-238; (year of pub. sufficiently earlier than effective US filing date and any foreign priority date) 1994.

Blank et al.; Do electromagnetic fields interact directly with DNA?; Bioelectromagnetics; vol. 18(2); pp. 111-115; (year of pub. sufficiently earlier than effective US filing date and any foreign priority date) 1997.

Blumenthal et al.; Effects of low-intensity AC and/or DC electromagnetic fields on cell attachment and induction of apoptosis; Bioelectromagnetics; vol. 18(3); pp. 264-272; (year of pub. sufficiently earlier than effective US filing date and any foreign priority date) 1997.

Borbely et al.; Pulsed high-frequency electromagnetic field affects human sleep and sleep electroencephalogram. Neurosci Lett 275, 207-10 (Nov. 19, 1999).

Bracken et al.; Administration of methylprednisolone for 24 or 48 hours or tirilazad mesylate for 48 hours in the treatment of acute spinal cord injury. Results of the Third National Acute Spinal Cord Injury Randomized Controlled Trial. National Acute Spinal Cord Injury Study. Jama 277, 1597-604 (May 28, 1997).

Bredt, D. S.; Nitric oxide signaling specificity-the heart of the problem. J Cell Sci 116, 9-15 (Jan. 2003).

Brighton et al.; Signal transduction in electrically stimulated bone cells. J Bone Joint Surg Am 83-A, 1514-23 (Oct. 2001).

Brighton, C. T.; The treatment of non-unions with electricity. J Bone Joint Surg Am 63, 847-51 (Jun. 1981).

Brooks et al.; Magnetic resonance spectroscopy in traumatic brain injury. J Head Trauma Rehabil 16, 149-64 (Apr. 2001).

Burton, T.; New Test for Brain Injury on Horizon, The Wall Street Journal, New York, (Jul. 20, 2010).

(56) References Cited

OTHER PUBLICATIONS

Cain; Stimulating Treatment; Orthopedic Technology Review; vol. 4; No. 4; pp. 31-34; Jul.-Aug. 2002.
Cammermeyer, J.; I. An evaluation of the significance of the "dark" neuron. Ergeb Anat Entwicklungsgesch 36, 1-61 (year of publication is sufficiently earlier than the effective U.S. filing date and any foreign priority date) (1962).
Canals et al.; Neurotrophic and neurotoxic effects of nitric oxide on fetal midbrain cultures. J Neurochem 76, 56-68 (Jan. 2001).
Canseven et al.; Effects of ambient ELF magnetic fields: variations in electrolyte levels in the brain and blood plasma; Gazi Tip Dergisi / Gazi Medical Journal; 16(3); pp. 121-127; Sep. 2005.
Casper et al.; Dopaminergic neurons associate with blood vessels in neural transplants. Exp Neurol 184, 785-93 (Dec. 2003).
Casper et al.; Enhanced vascularization and survival of neural transplants with ex vivo angiogenic gene transfer. Cell Transpl. 11, 331-349 (year of publication is sufficiently earlier than the effective U.S. filing date and any foreign priority date) (2002).
Cederberg et al.; What has inflammation to do with traumatic brain injury? Childs Nerv Syst 26, 221-6 (Feb. 2010).
Cernak et al.; Cognitive deficits following blast injury-induced neurotrauma: possible involvement of nitric oxide. Brain Inj 15, 593-612 (Jul. 2001).
Cernak et al.; Traumatic brain injury: an overview of pathobiology with emphasis on military populations. J Cereb Blood Flow Metab 30, 255-66 (Feb. 2010).
Cernak et al.; Ultrastructural and functional characteristics of blast injury-induced neurotrauma. J Trauma 50, 695-706 (Apr. 2001).
Chiabrera et al.; Bioelectromagnetic Resonance Interactions: Endogenous Field and Noise. In "Interaction Mechanisms of Low-Level Electromagnetic Fields in Living Systems." Oxford University Press. 164.179; Dec. 1992.
Chiabrera et al.; Effect of Lifetimes on Ligand Binding Modelled by the Density Operator; Bioelectrochemistry and Bioenergetics; vol. 30; pp. 35-42; Mar. 1993.
Chiabrera et al.; Quantum dynamics of ions in molecular crevices under electromagnetic exposure; (Brighton C, Pollak S, editors); Electromagnetics in biology and medicine; San Francisco, USA; San Francisco Press; pp. 21-26; Jun. 1991.
Chiabrera et al.; The role of the magnetic field in the EM interaction with ligand binding; In: "Mechanistic Approaches to Interaction of Electric and Electromagnetic Fields With Living Systems;" Blank, Findl (eds); New York; Plenum Press; pp. 79-95; Oct. 31, 1987.
Ciani et al.; Akt pathway mediates a cGMP-dependent survival role of nitric oxide in cerebellar granule neurones. J Neurochem 81, 218-28 (Apr. 2002).
Clapham, D.; Calcium signaling; Cell; vol. 80; pp. 259-268; Jan. 27, 1995.
Clausen et al.; Neutralization of interleukin-1? modifies the inflammatory response and improves histological and cognitive outome following traumatic brain injury in mice. European Journal of Neuroscience; vol. 30; pp. 385-396; Aug. 30, 2009.
Colbert et al.; Magnetic mattress pad use in patients with fibromyalgia: A randomized double-blind pilot study; J Back Musculoskeletal Rehab; vol. 13(1); 19-31; Jan. 1999.
Collacott et al.; Bipolar permanent magnets for the treatment of low back pain: A pilot study; JAMA; vol. 283; No. 10; pp. 1322-1325; Mar. 8, 2000.
Colomer et al.; Physiological roles of the Ca2+/CaM-dependent protein kinase cascade in health and disease. Subcell Biochem 45, 169-214 (year of publication is sufficiently earlier than the effective U.S. filing date and any foreign priority date) (2007).
Cook et al.; Resting EEG is affected by exposure to a pulsed ELF magnetic field. Bioelectromagnetics 25, 196-203 (Apr. 2004).
Cook et al.; The effects of pulsed, high-frequency radio waves on the rate of osteogenesis in the healing of extraction wounds in dogs; Oral Sug.; 32(6); (Dec. 1971).
Cork et al.; Computer-aided analysis of polarized neurite growth. Effects of applied electrical fields on neuronal development. J Neurosci Methods 32, 45-54 (Apr. 1990).

Courtney et al.; A thoracic mechanism of mild traumatic brain injury due to blast pressure waves. Med Hypotheses 72, 76-83 (Jan. 2009).
Cox, J.; Interactive Properties of Calmodulin; Biochem J.; vol. 249(3); pp. 621-629; Feb. 1, 1988.
Csuka et al.; IL-10 levels in cerebrospinal fluid and serum of patients with severe traumatic brain injury: relationship to IL-6, TNF-alpha, TGF-beta1 and blood-brain barrier function. J Neuroimmunol 101, 211-21 (Nov. 1999).
Czosnyka, et al.; Montoring and Interpretation of Intracranial Pressure. J. Neurol Neurosurg Psychiatry; vol. 75, 813-821; (Jun. 2004).
De Olmos et al.; Use of an amino-cupric-silver technique for the detection of early and semiacute neuronal degeneration caused by neurotoxicants, hypoxia, and physical trauma. Neurotoxicol Teratol 16, 545-61 (Nov. 1994).
Dixon et al.; A controlled cortical impact model of traumatic brain injury in the rat. J Neurosci Methods 39, 253-62 (Oct. 1991).
Dixon et al.; A fluid percussion model of experimental brain injury in the rat. J Neurosurg 67, 110-9 (Jul. 1987).
Edmonds, D.; Larmor precession as a mechanism for the detection of static and alternating magnetic fields; Bioelectrochemistry and Bioenergetics; vol. 30; pp. 3-12; Mar. 1993.
Edwards et al.; Final results of MRC CRASH, a randomised placebo controlled trial of intravenous corticosteroid in adults with head injury-outcomes at 6 months. Lancet 365, 1957-9 (Jun. 2005).
Elder et al.; Blast-related mild traumatic brain injury: mechanisms of injury and impact on clinical care. Mt Sinai J Med 76, 111-8 (Apr. 2009).
Elder et al.; Increased locomotor activity in mice lacking the low-density lipoprotein receptor. Behav Brain Res 191, 256-65 (Aug. 2008).
Engström, S.; Dynamic properties of Lednev's parametric resonance mechanism; Bioelectromagnetics; vol. 17(1); pp. 58-70; (year of pub. sufficiently earlier than effective US filing date and any foreign priority date) 1996.
Fabre et al.; Antidepressant efficacy and cognitive effects of repetitive transcranial magnetic stimulation in vascular depression: an open trial. Int J Geriatr Psychiatry 19, 833-42 (Sep. 2004).
Farndale et al.; The action of pulsed magnetic fields on cyclic AMP levels in cultured fibroblasts. Biochim Biophys Acta 881, 46-53 (Mar. 19, 1986).
Farrarelli et al.; Breakdown in cortical effective connectivity during midazolam-induced loss of consciousness. Proc Natl Acad Sci U S A 107, 2681-6 (Feb. 9, 2010).
Fassbender et al.; Temporal profile of release of interleukin-1beta in neurotrauma. Neurosci Lett 284, 135-8 (Apr. 2000).
Faul et al.; Traumatic brain injury in the United States (Emergency department visits, hospitalization and deaths 2002-2006); U.S. Dept. of Health and Human Services, 74 pgs.; Mar. 2010.
Fetler et al.; Brain under surveillance: the microglia patrol. Science 309, 392-3 (Jul. 15, 2005).
Fitzsimmons et al.; A pulsing electric field (PEF) increases human chondrocyte proliferation through a transduction pathway involving nitric oxide signaling. J Orthop Res 26, 854-9 (Jun. 2008).
Fitzsimmons et al.; Combined magnetic fields increase net calcium flux in bone cells. Calcif. Tiss. Intl.; vol. 55; pp. 376-380; Nov. 1994.
Foda et al.; A new model of diffuse brain injury in rats. Part II: Morphological characterization. J Neurosurg 80, 301-13 (Feb. 1994).
Foley-Nolan et al.; Pulsed high frequency (27MHz) electromagnetic therapy for persistent neck pain. A double blind, placebo-controlled study of 20 patients. Orthopedics 13, 445-51 (Apr. 1990).
Friedman et al.; Quantitative proton MRS predicts outcome after traumatic brain injury. Neurology 52, 1384-91 (Apr. 1999).
Fukada et al.; On the piezoelectric effect of bone. J Phys Soc Japan 12(10), 1158-1162 (Oct. 1957).
Gaetz, M.; The neurophysiology of brain injury. Clin Neurophysiol 115, 4-18 (Jan. 2004).
Garthwaite et al.; Cyclic GMP and cell death in rat cerebellar slices. Neuroscience 26, 321-6 (Jul. 1988).
Gasparovic et al.; Decrease and recovery of N-acetylaspartate/creatine in rat brain remote from focal injury. J Neurotrauma 18, 241-6 (Mar. 2001).

(56) References Cited

OTHER PUBLICATIONS

Ghirnikar et al.; Inflammation in traumatic brain injury: role of cytokines and chemokines. Neurochem Res 23, 329-40 (Mar. 1998).
Ginsberg, A. J.; Ultrashort radio waves as a therapeutic agent. Med Record 140, 651-653 (Dec. 19, 1934).
Glass et al.; Mechanisms underlying inflammation in neurodegeneration. Cell 140, 918-34 (Mar. 19, 2010).
Goligorsky et al.; Relationships between caveolae and eNOS: everything in proximity and the proximity of everything; Am J Physiol Renal Physiol; 283; pp. F1-F10; Jul. 2002.
Gona et al.; Effects of 60 Hz electric and magnetic fields on the development of the rat cerebellum. Bioelectromagnetics 14, 433-47 (year of publication is sufficiently earlier than the effective U.S. filing date and any foreign priority date) (1993).
Goodwin et al.; A double-blind study of capacitively coupled electrical stimulation as an adjunct to lumbar spinal fusions(printed from online source). Spine 24(13), 1349-1357 (Jul. 1999).
Graeber et al.; New expression of myelomonocytic antigens by microglia and perivascular cells following lethal motor neuron injury. J Neuroimmunol 27, 121-32 (May 1990).
Greenebaum et al.; Effects of pulsed magnetic fields on neurite outgrowth from chick embryo dorsal root ganglia. Bioelectromagnetics 17, 293-302 (year of publication is sufficiently earlier than the effective U.S. filing date and any foreign priority date) (1996).
Halle, B.; On the cyclotron resonance mechanism for magnetic field effects on transmembrane ion conductivity; Bioelectromagnetics; vol. 9(4); pp. 381-385; (year of pub. sufficiently earlier than effective US filing date and any foreign priority date) 1988.
Hart, F.; A quantum mechanical model for bioelectromagnetic resonance phenomena; J Bioelectr; vol. 9; pp. 1-7; Jan. 1990.
Hellmich et al.; Dose-dependent neuronal injury after traumatic brain injury; Brain Research; 1044; pp. 144-154 (May 2005).
Hutchinson et al.; Inflammation in human brain injury: intracerebral concentrations of IL-1alpha, IL-1beta, and their endogenous inhibitor IL-1ra. J Neurotrauma 24, 1545-57 (Oct. 2007).
Ignarro et al.; Heme-dependent activation of guanylate cyclase by nitric oxide: a novel signal transduction mechanism. Blood Vessels 28, 67-73 (Nov.-Dec. 1991).
Ito et al.; Characterization of edema by diffusion-weighted imaging in experimental traumatic brain injury. J Neurosurg 84, 97-103 (Jan. 1996).
Itoh et al.; Accelerated wound healing of pressure ulcers by pulsed high peak power electromagnetic energy (Diapulse). Decubitus 4(1), pp. 24-25, 29-30, 32 & 34 (Feb. 1991).
Jackson et al.; The demonstration of new human brain-specific proteins by high-resolution two-dimensional polyacrylamide gel electrophoresis. J Neurol Sci 49, 429-38; (Mar. 1981).
Jenrow et al.; Weak ELF magnetic field effects on hippocampal rhythmic slow activity. Exp Neurol 153, 328-34 (Oct. 1998).
Johansson, et al.; Brij 58, a polyoxethylene acyl ether, creates membrane vesicles of uniform sidedness: A new tool to obtain inside-out (cytoplasmic side-out) plasma membrane vesicle; Plant J.; vol. 7(1); pp. 165-173; Jan. 1995.
Jokela et al.; Assessment of the magnetic field exposure due to the battery current of digital mobile phones. Health Phys 86, 56-66 (Jan. 2004).
Jones et al.; Low energy time varying electromagnetic field interactions with cellular control mechanisms; In: fMechanistic approaches to interactions of electric and electromagnetic fields with living systemsf; Blank, Findl (eds); Plenum Press; NY; pp. 389-397; Oct. 31, 1987.
Jortner, B. S.; The return of the dark neuron. A histological artifact complicating contemporary neurotoxicologic evaluation. Neurotoxicology 27, 628-34 (Jul. 2006).
Kamm et al.; The effect of traumatic brain injury upon the concentration and expression of interleukin-1beta and interleukin-10 in the rat. J Trauma 60, 152-7 (Jan. 2006).
Kanje et al.; Pretreatment of rats with pulsed electromagnetic fields enhances regeneration of the sciatic nerve. Bioelectromagnetics 14, 353-9 (year of publication is sufficiently earlier than the effective U.S. filing date and any foreign priority date) (1993).
Kimura et al.; Reciprocol regulation between nitric oxide and vascular endothelial growth factor in angiogenesis; Acta Biochimica Polonica; vol. 50, No. 1; pp. 49-59; (year of publication is sufficiently earlier than the effective U.S. filing date and any foreign priority date) 2003.
Kingham et al.; Microglial secreted cathepsin B induces neuronal apoptosis. J Neurochem 76, 1475-84 (Mar. 2001).
Kjellbom et al.; Preparation and polypeptide composition of chlorophyll-free plasma membranes from leaves of light-grown spinach and barley; Physiol Plant; vol. 62; pp. 501-509; Dec. 1984.
Kloth et al.; Effect of Pulsed Radio Frequency Stimulation on Wound Healing: A Double-Blind Pilot Clinical Study; in "Electricity and Magnetism in Biology and Medicine"; Bersani F, ed Plenum, New York; pp. 875-878; (year of pub. sufficiently earlier than effective US filing date and any foreign priority date) 1999.
Knowles et al.; Nitric oxide synthases in mammals. Biochem J 298, 249-58 (Mar. 1994).
Koch, et al.; Interaction between weak low-frequency magnetic fields and cell membranes; Bioelectromagnetics; vol. 24(6); pp. 39-402; Sep. 2003.
Körner et al.; Surface properties of right side-out plasma membrane vesicles isolated from barley roots and leaves; Plant Physiol.; vol. 79(1); pp. 72-79; Sep. 1985.
Kossmann et al.; Intrathecal and serum interleukin-6 and the acute-phase response in patients with severe traumatic brain injuries. Shock 4, 311-7 (Nov. 1995).
Kramarenko et al.; Effects of high-frequency electromagnetic fields on human EEG: a brain mapping study. Int J Neurosci 113, 1007-19 (Jul. 2003).
Lai et al.; Magnetic-field-induced DNA strand breaks in brain cells of the rat. Environ Health Perspect 112, 687-94 (May 2004).
Langlois et al.; The epidemiology and impact of traumatic brain injury: a brief overview. J Head Trauma Rehabil 21, 375-8 (Aug. 2006).
Lansdown et al.; Sequential changes in trace metal, metallothionein and calmodulin concentrations in healing skin wounds; J. Anat.; vol. 195(Pt 3); pp. 375-386; Oct. 1999.
Larsson et al.; Isolation of highly purified plant plasma membranes and separation of inside-out and rightside-out vesicles; Methods Enzymol; vol. 228; pp. 451-469; (year of pub. sufficiently earlier than effective US filing date and any foreign priority date) 1994.
Lednev, V.; Possible mechanism for the effect of weak magnetic fields on biological systems: Correction of the basic expression and its consequences; In: Electricity and magnetism in biology and medicine Blank (eds.); San Francisco, CA; San Francisco Press, Inc.; pp. 550-552; Oct. 1993.
Lednev, V.; Possible mechanism for the influence of weak magnetic fields on biological systems; Bioelectromagnetics; vol. 12; pp. 71-75; (year of publication is sufficiently earlier than the effective U.S. filing date and any foreign priority date) 1991.
LeDoux, J.; Emotion: clues from the brain. Annu Rev Psychol 46, 209-35 (Jan. 1995).
Lee et al.; Nitric oxide in the healing wound: a time-course study. J Surg Res 101, 104-8 (Nov. 2001).
Lee et al.; Pulsed magnetic and electromagnetic fields in experimental achilles tendonitis in the rat: a prospective randomized study. Arch Phys Med Rehabil 78, 399-404 (Apr. 1997).
Lescot et al.; Temporal and regional changes after focal traumatic brain injury. J Neurotrauma 27, 85-94 (Jan. 2010).
Liboff, et al.; Experimental evidence for ion cyclotron resonance mediation of membrane transport; In: Blank, Findl (eds.); Mechanical approaches to interactions of electric and electromagnetic fields with living systems; Blank, Findl (eds.); New York; Plenum Press; pp. 281-296; Oct. 31, 1987.
Liboff, et al.; Geomagnetic cyclotron resonance in living cells; J Biol Phys; vol. 13(4); pp. 99-102; Dec. 1985.
Liboff, et al.; Kinetics of channelized membrane ions in magnetic fields; Bioelectromagnetics; vol. 9(1); pp. 39-51; (year of pub. sufficiently earlier than effective US filing date and any foreign priority date) 1988.

(56) References Cited

OTHER PUBLICATIONS

Lighthall, J. W.; Controlled cortical impact: a new experimental brain injury model. J Neurotrauma 5, 1-15 (year of publication is sufficiently earlier than the effective U.S. filing date and any foreign priority date) (1988).
Likic et al.; Dynamics of Ca2+-saturated Calmodulin D129N Mutant Studied by Multiple Molecular Dynamics Simulations; Protein Sci; vol. 12(10); pp. 2215-2229; Oct. 2003.
Lincoln et al.; Low frequency of pathogenic mutations in the ubiquitin carboxy-terminal hydrolase gene in familial Parkinson's disease. Neuroreport 10, 427-9 (Feb. 1999).
Ling et al.; Explosive blast neurotrauma. J Neurotrauma 26, 815-25 (Jun. 2009).
Linovitz et al.; Combined magnetic fields accelerate and increase spine fusion: a double-blind, randomized, placebo controlled study(printed from online source). Spine 27, 1383-1389 (Jul. 2002).
Liu et al.; Ubiquitin C-terminal hydrolase-L1 as a biomarker for ischemic and traumatic brain injury in rats (Author Manuscript). Eur J Neurosci 31(4), 722-32 (Feb. 2010).
Louin et al.; Selective inhibition of inducible nitric oxide synthase reduces neurological deficit but not cerebral edema following traumatic brain injury. Neuropharmacology 50, 182-90 (Feb. 2006).
Lukas, T.; A Signal Transduction Pathway Model Prototype II: Application to Ca2+-Calmodulin Signaling and Myosin Light Chain Phosphorylatiori; Biophysical Journal; vol. 87(3); pp. 1417-1425; Sep. 2004.
Maas et al.; Moderate and severe traumatic brain injury in adults. Lancet Neurol 7, 728-41 (Aug. 2008).
Maas et al.; Prognosis and clinical trial design in traumatic brain injury: the Impact study. J Neurotrauma 24, 232-8 (Feb. 2007).
Maas et al.; Why have recent trials of neuroprotective agents in head injury failed to how convincing efficacy? A pragmatic analysis and theoretical considerations. (printed from online source) Neurosurgery 44, 1286-98 (Jun. 1999).
Madhusoodanan et al.; NO-cGMP signaling and regenerative medicine involving stem cells. Neurochem Res 32, 681-94 (Apr.-May 2007).
Maeda et al.; Effect of water on piezoelectric, dielectric, and elastic properties of bone; Biopolymers 21(10); 2055-2068 (Oct. 1982).
Man, et al.; The influence of permanent magnetic field therapy on wound healing in suction lipectomy patients: A double-blind study; Plastic and Reconstructive Surgery; vol. 104(7); pp. 2261-2296; Dec. 1999 (printed Jul. 17, 2010).
Markov, et al.; Weak static magnetic field modulation of myosin phosphorylation in a cell-free preparation: Calcium dependence; Bioelectrochemistry and Bioenergetics; vol. 43(2); pp. 233-238; Aug. 1997.
Marmarou et al.; A new model of diffuse brain injury in rats. Part I: Pathophysiology and biomechanics. J Neurosurg 80, 291-300 (Feb. 1994).
Martin et al.; Parkinson's disease alpha-synuclein transgenic mice develop neuronal mitochondrial degeneration and cell death. J Neurosci 26, 41-50 (Jan. 2006).
McDonald, F.; Effect of static magnetic fields on osteoblasts and fibroblasts in-vitro; Bioelectromagnetics; vol. 14(3); pp. 187-196; (year of pub. sufficiently earlier than effective US filing date and any foreign priority date) 1993.
McFarlane et al.; Changes in neurite outgrowth but not in cell division induced by low EMF exposure: influence of field strength and culture conditions on responses in rat PC12 pheochromocytoma cells. Bioelectrochemistry 52, 23-8 (Sep. 2000).
McIntosh et al.; Traumatic brain injury in the rat: characterization of a lateral fluid-percussion model. Neuroscience 28(1), 233-44 (year of publication is sufficiently earlier than the effective U.S. filing date and any foreign priority date) (1989).
McIntosh et al.; Traumatic brain injury in the rat: characterization of a midline fluid-percussion model. Cent Nerv Syst Trauma 4, 119-34 (year of publication is sufficiently earlier than the effective U.S. filing date and any foreign priority date) (1987).

McLean, et al.; Blockade of sensory neuron action potentials by a static magnetic field in the 10 mT range; Bioelectromagnetics; vol. 16(1); pp. 20-32; (year of pub. sufficiently earlier than effective US filing date and any foreign priority date) 1995.
McLeod, et al.; Dynamic characteristics of membrane ions in multifield configurations of low-frequency electromagnetic radiation; Bioelectromagnetics; vol. 7(2); pp. 177-189; (year of pub. sufficiently earlier than effective US filing date and any foreign priority date) 1986.
Mehler, et al.; Structural Dynamics of Calmodulin and Troponin C; Protein Engineering; vol. 4; No. 6; pp. 625-627; Aug. 1991.
Mellor, S.; The pathogenesis of blast injury and its management. Br J Hosp Med 39, 536-9 (Jun. 1988).
Mont et al.; Pulsed electrcial stimulation to defer TKA in patients with knee osteoarthritis; The Cutting Edge; 29(10); pp. 887-892 (Oct. 2006).
Mooney; A randomized double blind prospective study of the efficacy of pulsed electromagnetic fields for interbody lumbar fusions; Spine; vol. 15(7); pp. 708-715; Jul. 1990.
Morganti-Kossmann et al.; Production of cytokines following brain injury: beneficial and deleterious for the damaged tissue. Mol Psychiatry 2, 133-6 (Mar. 1997).
Morris et al.; Place navigation impaired in rats with hippocampal lesions. Nature 297, 681-3 (Jun. 1982).
Muehsam et al.; Lorentz Approach to Static Magnetic Field Effects on Bound Ion Dynamics and Binding Kinetics: Thermal Noise Considerations; Bioelectromagnetics; vol. 17(2); pp. 89-99; (year of pub. sufficiently earlier than effective US filing date and any foreign priority date) 1996.
Muehsam et al.; Weak Magnetic Field Modulation of Ion Dynamics in a Potential Well: Mechanistic and Thermal Noise Considerations; Bioelectrochem. & Bioenergetics; vol. 35; pp. 71-79; Nov. 1994.
Muehsam, et al.; The sensitivity of cells and tissues to exogenous fields: effects of target system initial state; Bioelectrochemistry and Bioenergetics; vol. 48(1); pp. 35-42; Feb. 1999.
Naldini et al.; Role of inflammatory mediators in angiogenesis. Curr Drug Targets Inflamm Allergy 4, 3-8 (Feb. 2005).
Nara, et al.; Fourier Transform Infrared Spectroscopic Study on the Ca2+-bound Coordination Structures of Synthetic Peptide Analogues of the Calcium-binding Site III of Troponin C; Biopolymers; vol. 82; issue 4; pp. 339-343; Jul. 2006.
Narayan et al.; Clinical trials in head injury (Author Manuscript). J Neurotrauma 19, 503-57 (May 2002).
Nauta et al.; Silver impregnation of degenerating axons in the central nervous system: a modified technic. Stain Technol 29, 91-3 (Mar. 1954).
Northington et al.; Early Neurodegeneration after Hypoxia-Ischemia in Neonatal Rat Is Necrosis while Delayed Neuronal Death Is Apoptosis. Neurobiol Dis 8, 207-19 (Apr. 2001).
Oda et al.; Magnetic field exposure saves rat cerebellar granule neurons from apoptosis in vitro. Neurosci Lett 365, 83-6 (Jul. 22, 2004).
Ohkubo et al.; Acute effects of static magnetic fields on cutaneous microcirculation in rabbits; In Vivo; vol. 11; pp. 221-226; May-Jun. 1997.
Okano et al.; Biphasic effects of static magnetic fields on cutaneous microcirculation in rabbits; Bioelectromagnetics; vol. 20(3); pp. 161-171; (year of publication is sufficiently earlier than the effective U.S. filing date and any foreign priority date) 1999.
Okie, S.; Traumatic brain injury in the war zone. N Engl J Med 352, 2043-7 (May 19, 2005).
Olbe et al.; The spinach plasma membrane Ca2þ pump is a 120-kDa polypeptide regulated by calmodulinbinding to a terminal region; Physiol Plantarum; vol. 103; pp. 35-44; May 1998.
Pantazis et al.; The nitric oxide-cyclic GMP pathway plays an essential role in both promoting cell survival of cerebellar granule cells in culture and protecting the cells against ethanol neurotoxicity. J Neurochem 70, 1826-38 (May 1998).
Papa et al.; Ubiquitin C-terminal hydrolase is a novel biomarker in humans for severe traumatic brain injury. Crit Care Med 38, 138-44 (Jan. 2010).

(56) References Cited

OTHER PUBLICATIONS

Pascual et al.; Time course of early metabolic changes following diffuse traumatic brain injury in rats as detected by (1)H NMR spectroscopy. J Neurotrauma 24, 944-59 (Jun. 2007).
Patino et al.; Pulsed electromagnetic fields in experimental cutaneous wound healing in rats. J Burn Care Rehabil 17, 528-31 (Nov./Dec. 1996).
Paylor et al.; Inbred strain differences in prepulse inhibition of the mouse startle response. Psychopharmacology (Berl) 132, 169-80 (Jul. 1997).
Pennington et al.; Pulsed, non-thermal, high-frequency electromagnetic energy (DIAPULSE) in the treatment of grade I and grade II ankle sprains. Mil Med 158, 101-4 (Feb. 1993).
Pfeffer et al.; Disturbed sleep/wake rhythms and neuronal cell loss in lateral hypothalamus and retina of mice with a spontaneous deletion in the ubiquitin carboxyl-terminal hydrolase L1 gene. Neurobiol Aging 33, 393-403, in press, Epub ahead of print (Apr. 2010).
Pilla et al.; EMF signals and ion/ligand binding kinetics:prediction of bioeffective waveform parameters; Bioelectrochemistry and Bioenergetics; vol. 48(1); pp. 27-34; Feb. 1999.
Pilla et al.; Gap junction impedance tissue dielectrics and thermal noise limits for electromagnetic field bioeffects; Bioelectrochemistry and Bioenergetics; vol. 35; pp. 63-69; Nov. 1994.
Pilla, A.; Mechanisms and therapeutic applications of time-varying and static magnetic fields; In: Biological and Medical Aspects of Electromagnetic Fields (eds. Barnes et al.) CRC Press, Boca Raton FL, 351-411 (Oct. 2006).
Pilla; Electrochemical information and energy transfer in vivo; Proc. 7th IECEC;Washington, D.C.; American Chemical Society; pp. 761-764; (year of publication is sufficiently earlier than the effective U.S. filing date and any foreign priority date) 1972.
Pilla; Electrochemical information transfer at living cell membrane; Ann. N.Y.Acad. Sci.; vol. 238; p. 149-170; Oct. 1974.
Pilla; Low-intensity electromagnetic and mechanical modulation of bone growth and repair: are they equivalent?; Journal of Orthopedic Science; vol. 7(3); pp. 420-428; (year of pub. sufficiently earlier than effective US filing date and any foreign priority date) 2002.
Pilla; State of the art in electromagnetic therapeutics: soft tissue applications; Electricity and Magnetism in Biology and Medicine; Bersani (ed.); Kluwer Academic/Plenum Publishers; pp. 871-874; (year of pub. sufficiently earlier than effective US filing date and any foreign priority date) 1999.
Pilla; Weak time-varying and static magnetic fields: from Mechanisms to therapeutic applications; Biological Effects of Electro Magnetic Fields; P. Stavroulakis, ed. Springer Verlag; pp. 34-75; (year of pub. sufficiently earlier than effective US filing date and any foreign priority date) 2003.
Pineros et al.; Calcium channels in higher plant cells: Selectivity, regulation, and pharmacology; J Exp Bot; vol. 48; special issue; pp. 551-577; Mar. 1997.
Pirozzoli et al.; Effects of 50 Hz electromagnetic field exposure on apoptosis and differentiation in a neuroblastoma cell line. Bioelectromagnetics 24, 510-6 (Oct. 2003).
Ramundo-Orlando, et al.; Effect of Low Frequency, Low Amplitude Magnetic Fields on the Permeability of Cationic Liposomes Entrapping Carbonic Anhydrase I. Evidence for Charged Lipid Involvement; Bioelectromagnetics; vol. 21; pp. 491-498; Oct. 2000.
Reale et al.; Modulation of MCP-1 and iNOS by 50-Hz sinusoidal electromagnetic field. Nitric Oxide 15, 50-7 (Aug. 2006).
Ren et al.; Role of interleukin-1? during pain and inflammation (Author Manuscript). Brain Res Rev 60, 57-64 (Apr. 2009).
Rich et al.; Chronic caloric restriction reduces tissue damage and improves spatial memory in a rat model of traumatic brain injury. J Neurosci Res 88, 2933-9 (Oct. 2010).
Rogers et al.; Behavioral and functional analysis of mouse phenotype: SHIRPA, a proposed protocol for comprehensive phenotype assessment. Mamm Genome 8, 711-3 (Oct. 1997).

Rohde et al.; Effects of pulsed electromagnetic fields on interleukin-1 beta and postoperative pain: a double-blind, placebo-controlled, pilot study in breast reduction patients. Plast Reconstr Surg 125, 1620-9 (1-10) (Jun. 2010).
Ryaby et al.; The role of insulin-like growth factor in magnetic field regulation of bone formation. Bioelectrochem. Bioenergetics; vol. 35(1-2); pp. 87-91; Nov. 1994.
Sagan, L.; Epidemiological and laboratory studies of power frequency electric and magnetic fields; JAMA; vol. 268(5); pp. 625-629; Aug. 5, 1992.
Saljo et al.; Exposure to short-lasting impulse noise causes microglial and astroglial cell activation in the adult rat brain. Pathophysiology 8, 105-111 (Dec. 2001).
Saljo et al.; Low-level blast raises intracranial pressure and impairs cognitive function in rats: prophylaxis with processed cereal feed. J Neurotrauma 27, 383-9 (Feb. 2010).
Salzberg et al.; The effects of non-thermal pulsed electromagnetic energy on wound healing of pressure ulcers in spinal cord-injured patients: a randomized, double-blind study. Ostomy Wound Manage 41, 42-4, 46, 48 passim (Apr. 1995).
Sandyk, R.; Treatment with AC pulsed electromagnetic fields improves olfactory function in Parkinson's disease. Int J Neurosci 97, 225-33 (Apr. 1999).
Sapolsky; Glucocorticoid toxicity in the hippocampus: temporal aspects of neuronal vulnerability. Brain Res 359, 300-5 (Dec. 16, 1985).
Sarimov, et al.; Exposure to ELF Magnetic Field Tuned to Zn Inhibits Growth of Cancer Cells. Bioelectromagnetics; vol. 26; No. 8; pp. 631-638; Dec. 2005.
Sauerland et al.; Risks and benefits of preoperative high dose methylprednisolone in surgical patients: a systematic review. Drug Saf 23, 449-61 (Nov. 2000).
Schmued et al.; Fluoro-Jade: a novel fluorochrome for the sensitive and reliable histochemical localization of neuronal degeneration. Brain Res 751, 37-46 (Mar. 1997).
Seegers et al.; Activation of signal-transduction mechanisms may underlie the therapeutic effects of an applied electric field. Med Hypotheses 57, 224-30 (Aug. 2001).
Shupak et al.; Human exposure to a specific pulsed magnetic field: effects on thermal sensory and pain thresholds. Neurosci Lett 363, 157-62 (Jun. 10, 2004).
Sisken et al.; Prospects on clinical applications of electrical stimulation for nerve regeneration. J Cell Biochem 52, 404-409 (Apr. 1993).
Sisken, et al.; Static magnetic fields and nerve regeneration (presentation abstract); Bioelectromagnetics Society; 21st Ann Meeting, Long Beach, Jun. 20-24, 1999.
Slepko et al.; Progressive activation of adult microglial cells in vitro. Glia 16, 241-46 (Mar. 1996).
Smith, S.; Calcium cyclotron resonance and diatom mobility; Bioelectromagnetics; vol. 8; pp. 215-227; (year of publication is sufficiently earlier than the effective U.S. filing date and any foreign priority date) 1987.
Stahel et al.; The role of the complement system in traumatic brain injury. Brain Res Brain Res Rev 27, 243-56 (Jul. 1998).
Steinberg et al.; Osteonecrosis of the Femoral Head. Results of core decompression and grafting with and without electrical stimulation. Clin Orthop, 199-208 (Dec. 1989).
Teleman et al.; Kinetics of Ca2+ binding to calmodulin and its tryptic fragments studied by 43Ca-NMR. Biochim Biophys Acta 873, 204-13 (Sep. 1986).
Tehranian et al.; Improved recovery and delayed cytokine induction after closed head injury in mice with central overexpression of the secreted isoform of the interleukin-1 receptor antagonist. J Neurotrauma 19, 939-51 (Aug. 2002).
Terpolilli et al.; The novel nitric oxide synthase inhibitor 4-amino-tetrahydro-L-biopterine prevents brain edema formation and intracranial hypertension following traumatic brain injury in mice. J Neurotrauma 26, 1963-75 (Nov. 2009).
Thurman et al.; The epidemiology of sports-related traumatic brain injuries in the United States: recent developments. J Head Trauma Rehabil 13, 1-8 (Apr. 1998).

(56) References Cited

OTHER PUBLICATIONS

Trillo et al.; Magnetic fields at resonant conditions for the hydrogen ion affect neurite outgrowth in PC-12 cells: a test of the ion parametric resonance model. Bioelectromagnetics 17, 10-20 (year of publication is sufficiently earlier than the effective U.S. filing date and any foreign priority date) (1996).
Unterberg et al.; Edema and brain trauma. Neuroscience 129(4), 1021-9 (year of publication is sufficiently earlier than the effective U.S. filing date and any foreign priority date) (2004).
Valbona, et al.; Response of pain to static magnetic fields in post-polio patients: A doubleblind pilot study; Arch. Phys. Med. Rehabil.; vol. 78(11); pp. 1200-1203; Nov. 1997.
Vianale et al.; Extremely low frequency electromagnetic field enhances human keratinocyte cell growth and decreases proinflammatory chemokine production. Br J Dermatol 158(6), 1189-96 (Jun. 2008).
Weaver, et al.; The response of living cells to very weak electric fields: The thermal noise limit; Science; vol. 247, No. 4941; pp. 459-462; Jan. 1990.
Weinstein, et al.; Ca2+-Binding and Structural Dynamics in the functions of Calmodulin; Ann. Rev. Physiol; vol. 56; pp. 213-236; Mar. 1994.
Weintraub, M.; Magnetic bio-stimulation in painful diabetic peripheral neuropathy: a novel intervention R a randomized double-placebo crossover study; Am J Pain Manag; vol. 9; pp. 8-17; Jan. 1, 1999.
Weissman et al.; Activation and inactivation of neuronal nitric oxide synthase: characterization of Ca(2+)-dependent [125I]Calmodulin binding. Eur J Pharmacol 435, 9-18 (Jan. 2002).
Wenk, G.; The nucleus basalis magnocellularis cholinergic system: one hundred years of progress; Neurobiology of Learning and Memory; 67(2); 85-95 (Mar. 1997).
Williams et al.; Characterization of a new rat model of penetrating ballistic brain injury. J Neurotrauma 22, 313-31 (Feb. 2005).
Yasuda, I.; Part III. Clinical Studies: Mechanical and electrical callus; Annals of the New York Academy of Sciences; vol. 238; pp. 457-465 (Oct. 1974).
Yu et al.; Effects of 60 Hz electric and magnetic fields on maturation of the rat neopallium. Bioelectromagnetics 14, 449-58 (year of publication is sufficiently earlier than the effective U.S. filing date and any foreign priority date) (1993).
Yumoto, et al.; Coordination Structures of Ca2+ and Mg2+ in Akazara Scallop Troponin C in Solution; Eur. J. Biochem; vol. 268(23); pp. 6284-6290; Dec. 2001.
Zaloshnja et al.; Prevalence of long-term disability from traumatic brain injury in the civilian population of the United States, 2005. J Head Trauma Rehabil 23, 394-400 (Nov./Dec. 2008).
Zdeblick; A prospective, randomized study of lumbar fusion: preliminary results; Spine; vol. 18; pp. 983-991; Jun. 15, 1993.
Zhadin, et al.; Frequency and Amplitude Windows in the Combined Action of DC and Low Frequency AC Magnetic Fields on Ion Thermal Motion in a Macromolecule: Theoretical Analysis; Bioelectromagnetics; vol. 26; issue 4; pp. 323-330; May 2005.
Zhadin, et al.; Ion Cyclotron Resonance in Biomolecules; Biomed Sci; vol. 1; pp. 245-250; (year of publication is sufficiently earlier than the effective U.S. filing date and any foreign priority date) 1990.
Zhadin, M.; Combined action of static and alternating magnetic fields on ion motion in a macromolecule; Theoretical aspects; Bioelectromagnetics; vol. 19(5); pp. 279-292; (year of pub. sufficiently earlier than effective US filing date and any foreign priority date) 1998.
Zhuang et al.; Electrical stimulation induces the level of TGF-B 1 mRNA in osteoblastic cells by amechanism involving calcium/calmodulin pathway; Biochem. Biophys. Res. Comm.; vol. 237;pp. 225-229; Aug. 18, 1997.
Ziebell et al.; Involvement of pro- and anti-inflammatory cytokines and chemokines in the pathophysiology of traumatic brain injury. Neurotherapeutics 7, 22-30 (Jan. 2010).
Zizic et al.; The treatment of osteoarthritis of the knee with pulsed electrical stimulation. J Rheumatol 22, 1757-61 (Sep. 1995).
Batchelor et al.; Exquisite sensititivity to subsecond, picomolar nitric oxide transients conferred on cells by guanylyl cyclase-coupled receptors; Proc. Natl. Acad. Sci. U.S.A.; 107(51); pp. 22060-22065; Dec. 21, 2010.
Binshtok et al.; Nociceptors are interleukin-1 beta sensors; J. Neurosci.; 28 (52); pp. 14062-14073; Dec. 24, 2008.
Bodian et al.; The visual analog scale for pain: clinical significance in postoperative patients; Anesthesiology; 95(6); pp. 1356-1361; Dec. 2001.
Coll et al.; Postoperative pain assessment tools in day surgery: literature review; J. Adv. Nurs.; 46(2); pp. 124-133; Apr. 2004.
Delle Monache et al.; Extremely low frequency electromagnetic fields (ELF-EMFs) induce in vitro angiogenesis process in human endothelial cells; Bioelectromagnetics; 29; pp. 640-648; Mar. 5, 2008.
Ha et al.; Nitric oxide prevents 6-hydroxydopamine induced apoptosis in PC12 cells through cGMP-dependent PI3 kinase/Akt activation; FASEB J.; 17(9); pp. 1036-1047; Jun. 2003.
Heden et al.; Effects of pulsed electromagnetic fields on postoperative pain: a double-blind randomized pilot study in breast augmentation patients; Aesthet. Plast. Surg.; 32; pp. 660-666; Jul. 2008.
Kehlet et al.; Evidence-based surgical care and the evolution of fast-track surgery; Ann. Surg.; 248(2); pp. 189-198; Aug. 2008.
Klit et al.; Central post-stroke pain: clinical characteristics, pathophysiology, and management; Lancet Neurol.; 8(9); pp. 857-868; Sep. 2009.
Liu et al.; Efficacy of continuous wound catheters delivering local anesthetic for postoperative analgesia: a quantitative and qualitative systematic review of randomized controlled trials; J. Am. Coll. Surg.; 203(6); pp. 914-932; Dec. 31, 2006.
Miller et al.; Role of Ca2+/calmodulinstimulated cyclic nucleotide phosphodiesterase 1 in mediating cardiomyocyte hypertrophy; Circ. Res.; 105(10); pp. 956-964; Nov. 6, 2009.
Mo et al.; Kinetics of a cellular nitric oxide/cGMP/phosphodiesterase-5 pathway; J. Biol. Chem.; 279(25); pp. 26149-26158; Jun. 18, 2004.
Neff; Using pulsed energy therapy for brain injury and concussion; The Headliner; vol. X; Issue 4; pp. 14; Fall 2008.
Roland et al.; Effects of pulsed magnetic energy on a microsurgically transferred vessel; Plast. Reconstr. Surg.; 105(4); pp. 1371-1374; Apr. 2000.
Strauch et al; Evidence-based use of pulsed electromagentic field therapy in clinical plastic surgery; Aesthetic Surg. J.; 29(2); pp. 135-143; Mar.-Apr. 2009.
Tepper et al.; Electromagnetic fields increase in vitro and in vivo angiogenesis through endothelial release of FGF-2; FASEB J.; 18(11); pp. 1231-1233; Aug. 2004.
Weber et al.; Pusled magnetic fields applied to a transferred arterial loop support the rat groin composite flap; Plast. Reconstr. Surg.; 114(5); pp. 1185-1189; Oct. 2004.
Werner et al.; Regulation of wound healing by growth factors and cytokines; Physiol. Rev.; 83(3); pp. 835-870; Jul. 2003.
Wikipedia; ISM band; 6 pages; retrieved Nov. 30, 2015 from the internet; ( https://en.wikipedia.org/w/index.php?title=ISM_band&oldid=690024749).
World Health Organization; Neurlogical disorders: publiic health challenges; © 2006; 231 pages; retrieved Oct. 26, 2015 from the internet; http://www.who.int/mental_health/neurology/neurological_disorders_report_web.pdf.
Pilla; U.S. Appl. No. 14/932,928 entitled "Method and apparatus for electromagnetic treatment of living systems," filed Nov. 4, 2015.

* cited by examiner

METHOD AND APPARATUS FOR ELECTROMAGNETIC ENHANCEMENT OF BIOCHEMICAL SIGNALING PATHWAYS FOR THERAPEUTICS AND PROPHYLAXIS IN PLANTS, ANIMALS AND HUMANS

CROSS REFERENCE TO RELATED APPLICATIONS

This application is a divisional of U.S. patent application Ser. No. 13/285,761, filed Oct. 31, 2011, entitled "METHOD AND APPARATUS FOR ELECTROMAGNETIC ENHANCEMENT OF BIOCHEMICAL SIGNALING PATHWAYS FOR THERAPEUTICS AND PROPHYLAXIS IN PLANTS, ANIMALS AND HUMANS", now U.S. Pat. No. 9,656,096, which claims the benefit under 35 U.S.C. § 119 of U.S. Patent Application No. 61/456,036, filed Oct. 29, 2010, entitled "METHOD AND APPARATUS FOR ELECTROMAGNETIC ENHANCEMENT OF BIOCHEMICAL SIGNALING PATHWAYS FOR THERAPEUTICS AND PROPHYLAXIS IN PLANTS, ANIMALS AND HUMANS", now expired. These applications are herein incorporated by reference in their entirety.

U.S. patent application Ser. No. 13/285,761 also claims priority as a continuation-in-part of U.S. patent application Ser. No. 12/819,956, filed Jun. 21, 2010, entitled "APPARATUS AND METHOD FOR ELECTROMAGNETIC TREATMENT", Publication No. US-2011-0112352-A1, now abandoned, which claims priority as a continuation-in-part to each of the following: U.S. patent application Ser. No. 12/772,002, filed Apr. 30, 2010, entitled "APPARATUS AND METHOD FOR ELECTROMAGNETIC TREATMENT OF PLANT, ANIMAL AND HUMAN TISSUE, ORGANS, CELLS AND MOLECULES", Publication No. US-2010-0222631-A1, now abandoned which is a continuation of U.S. patent application Ser. No. 11/003,108, filed Dec.3, 2004, entitled "APPARATUS AND METHOD FOR ELECTROMAGNETIC TREATMENT OF PLANT, ANIMAL, AND HUMAN TISSUE, ORGANS, CELLS, AND MOLECULES", now U.S. Pat. No. 7,744,524, which claims the benefit under 35 U.S.C. § 119 of U.S. Provisional Patent Application No. 60/527,327, filed Dec. 5, 2003, entitled "APPARATUS AND METHOD FOR ELECTROMAGNETIC TREATMENT OF PLANT, ANIMAL, AND HUMAN TISSUE, ORGANS, CELLS AND MOLECULES", now expired; U.S. patent application Ser. No. 11/114,666, filed Apr. 25, 2005, entitled "ELECTROMAGNETIC TREATMENT INDUCTION APPARATUS AND METHOD FOR USING SAME", now U.S. Pat. No. 7,740,574, which claims the benefit under 35 U.S.C. § 119 of U.S. Provisional Patent Application No. 60/564,887, filed Apr. 26, 2004, entitled "INDUCTION MEANS FOR THERAPEUTICALLY TREATING HUMAN AND ANIMAL CELLS, TISSUES AND ORGANS WITH ELECTROMAGNETIC FIELDS", now expired; U.S. patent application Ser. No. 11/110,000, filed Apr. 19, 2005, entitled "ELECTROMAGNETIC TREATMENT APPARATUS AND METHOD FOR ANGIOGENESIS MODULATION OF LIVING TISSUES AND CELLS", Publication No. US 2005-0251229 A1, now abandoned, which claims the benefit under 35 U.S.C. § 119 of U.S. Provisional Patent Application No. 60/563,104, filed Apr. 29, 2004, entitled "APPARATUS AND METHOD FOR THERAPEUTICALLY TREATING HUMAN AND ANIMAL CELLS, TISSUES AND ORGANS WITH ELECTROMAGNETIC FIELDS", now expired; U.S. patent application Ser. No. 11/369,308, filed Mar. 6, 2006, entitled "ELECTROMAGNETIC TREATMENT APPARATUS FOR AUGMENTING WOUND REPAIR AND METHOD FOR USING SAME", Publication No. US-2006-0212077-A1, now abandoned, which claims the benefit under 35 U.S.C. § 119 of U.S. Provisional Patent Application No. 60/658,967, filed Mar. 7, 2005, entitled "APPARATUS AND METHOD FOR THERAPEUTICALLY TREATING HUMAN, ANIMAL, AND PLANT CELLS, TISSUES, ORGANS, AND MOLECULES WITH ELECTROMAGNETIC FIELDS FOR WOUND REPAIR", now expired; U.S. patent application Ser. No. 11/369,309, filed Mar. 6, 2006, entitled "ELECTROMAGNETIC TREATMENT APPARATUS FOR ENHANCING PHARMACOLOGICAL, CHEMICAL AND TOPICAL AGENT EFFECTIVENESS AND METHOD FOR USING SAME", Publication No. US-2007-0026514-A1, now abandoned, which claims the benefit under 35 U.S.C. § 119 of U.S. Provisional Patent Application No. 60/658,968, filed Mar. 7, 2005, entitled "APPARATUS AND METHOD FOR TREATING HUMAN, ANIMAL AND PLANT CELLS, TISSUES, ORGANS AND MOLECULES WITH ELECTROMAGNETIC FIELDS BY ENHANCINGHTE EFFECTS OF PHARMACOLOGICAL, CHEMICAL, COSMETIC AND TOPICAL AGENTS", now expired; U.S. patent application Ser. No. 11/223,073, filed Sep. 10, 2005, entitled "INTEGRATED COIL APPARATUS FOR THERAPEUTICALLY TREATING HUMAN AND ANIMAL CELLS, TISSUES AND ORGANS WITH ELECTROMAGNETIC FIELDS AND METHOD FOR USING SAME", now U.S. Pat. No. 7,758,490; U.S. patent application Ser. No. 11/339,204, filed Jan. 25, 2006, entitled "SELF-CONTAINED ELECTROMAGNETIC APPARATUS FOR TREATMENT OF MOLECULES, CELLS, TISSUES, AND ORGANS WITHIN A CEREBROFACIAL AREA AND METHOD FOR USING SAME", Publication No. US-2007-0173904-A1, now abandoned; U.S. patent application Ser. No. 11/818,065, filed Jun. 12, 2007, entitled "ELECTROMAGNETIC APPARATUS FOR PROPHYLAXIS AND REPAIR OF OPHTHALMIC TISSUE AND METHOD FOR USING SAME", now Publication No. US-2008-0058793-A1, now abandoned, which claims the benefit under 35 U.S.C. § 119 of U.S. Provisional Patent Application No. 60/812,841, filed Jun. 12, 2006, entitled "APPARATUS AND METHOD FOR THERAPEUTICALLY TREATING HUMAN AND ANIMAL CELLS, TISSUES, ORGANS AND MOLECULES WITH ELECTROMAGNETIC FIELDS FOR TREATMENT OF DISEASES OF THE EYE AND PROPHYLACTIC TREATMENT OF THE EYE", now expired; U.S. patent application Ser. No. 11/903,294, filed Sep. 20, 2007, entitled "ELECTROMAGNETIC APPARATUS FOR RESPIRATORY DISEASE AND METHOD FOR USING SAME", Publication No. US-2008-0132971-A1, now abandoned, which claims the benefit under 35 U.S.C. § 119 of U.S. Provisional Patent Application No. 60/846,126, filed Sep. 20, 2006, entitled "APPARATUS AND METHOD FOR THE TREATMENT OF DISEASES OF THE LUNGS WITH ELECTROMAGNETIC FIELDS", now expired; and U.S. patent application Ser. No. 11/977,043, filed Oct. 22, 2007, entitled "APPARATUS AND METHOD FOR THE TREATMENT OF EXCESSIVE FIBROUS CAPSULE FORMATION AND CAPSULAR CONTRACTURE WITH ELECTROMAGNETIC FIELDS", Publication No. US-2013-0218238-A9, now abandoned, which claims the benefit under 35 U.S.C. § 119 of U.S. Provisional Patent Application No. 60/852,927, filed Oct. 20, 2006, entitled "APPARATUS AND METHOD FOR THE TREATMENT OF EXCESSIVE FIBROUS CAPSULE FORMATION AND CAPSULAR CONTRACTURE WITH ELECTROMAGNETIC FIELDS", now expired. These applications are herein incorporated by reference in their entirety.

INCORPORATION BY REFERENCE

All publications and patent applications mentioned in this specification are herein incorporated by reference to the same extent as if each individual publication or patent application was specifically and individually indicated to be incorporated by reference.

BACKGROUND

1. Field of the Invention

This invention pertains generally to a method and apparatus for in vitro and in vivo therapeutic and prophylactic treatment of plant, animal, and human molecules, cells, tissues, organs, portions of entire organisms and entire organisms. In particular, an embodiment according to the present invention pertains to use of non-thermal static and time-varying electromagnetic fields configured to accelerate the asymmetrical kinetics of the binding of intracellular ions to their respective buffers which regulate the biochemical signaling pathways living systems employ for growth, repair and maintenance. Another embodiment according to the present invention pertains to the non-thermal application of repetitive pulse bursts of sinusoidal, rectangular, chaotic or arbitrary waveform electromagnetic fields to instantaneously accelerate ion-buffer binding in signaling pathways in structures such as molecules, cells, tissues, organs, and entire organisms of plants, animals or humans using ultra lightweight portable coupling devices such as inductors and electrodes, driven by miniature signal generator circuitry that can be incorporated into an anatomical positioning device such as a dressing, bandage, compression bandage, compression dressing; knee, elbow, lumbar or cervical back, shoulder, foot, head, neck and other body portion wraps and supports; garments, footwear, gloves, and fashion accessories; mattress pads, seat cushions, beds, furniture; seats, beds, cushions and other body supports in cars, motorcycles, bicycles, buses, trains, airplanes, boats and ships.

Yet another embodiment according to the present invention pertains to application of sinusoidal, rectangular, chaotic or arbitrary waveform electromagnetic signals, having frequency components below about 100 GHz, configured to accelerate the binding of intracellular $Ca^{2+}$ to a buffer, such as calmodulin (hereinafter known as CaM), to enhance biochemical signaling pathways in target structures such as plant, animal and human molecules, cells, tissues, organs, portions of entire organisms and entire organisms. Signals configured according to embodiments of the present invention produce a net increase in a bound ion, such as $Ca^{2+}$ at CaM binding sites because the asymmetrical kinetics of Ca/CaM binding allows such signals to accumulate voltage induced at the ion binding site, thereby accelerating voltage-dependent ion binding. Examples of therapeutic and prophylactic applications of the present invention are modulation of biochemical signaling in anti-inflammatory pathways, modulation of biochemical signaling in cytokine release pathways, modulation of biochemical signaling in growth factor release pathways; chronic and acute musculoskeletal pain relief; edema and lymph reduction, anti-inflammatory, post-surgical and post-operative pain and edema relief, nerve, bone and organ pain relief, angina pain relief, increased local blood flow, microvascular blood perfusion, treatment of tissue and organ ischemia, cardiac tissue ischemia, brain tissue ischemia from stroke or traumatic brain injury, treatment of neurological injury and neurodegenerative diseases such as Alzheimer's and Parkinson's; wound repair, bone repair, tissue repair; osteoporosis treatment and prevention; degenerative bone disease treatment and prevention; angiogenesis, neovascularization; enhanced immune response; treatment of diabetes Types I and II; enhanced effectiveness of pharmacological agents; nerve regeneration, skeletal muscle regeneration, cardiac muscle regeneration; cancer treatment; prevention of apoptosis; modulation of heat shock proteins for prophylaxis and response to injury or pathology. An embodiment according to the present invention can also be used in conjunction with other therapeutic and prophylactic procedures and modalities such as heat, cold, light, ultrasound, mechanical manipulation, massage, physical therapy, vacuum assisted wound closure, wound dressings, orthopedic and other surgical fixation devices, and surgical interventions. Yet another embodiment according to the present invention can also be used in conjunction with all pharmacological agents. Another embodiment of the present invention can be used with imaging or non-imaging diagnostic procedures.

2. Discussion of Related Art

Bone growth stimulator (hereinafter known as BGS) electromagnetic fields are now part of the standard armamentarium of orthopedic practice worldwide for the treatment of recalcitrant bone fractures. Radio frequency signals, originally developed for deep tissue heating (diathermy), were shown to produce biological effects when applied at non-thermal levels using pulse-modulation techniques to produce pulsed radio frequency (hereinafter known as PRF) signals. At the cellular level, numerous studies demonstrate that BGS, PRF and other electromagnetic field (hereinafter known as EMF) signals modulate the release of growth factors and cytokines.

Stimulation of transforming growth factor beta ("TGF-β") messenger RNA ("mRNA") with EMF in a bone induction model in a rat has been shown. Studies have also demonstrated up regulation of TGF-β mRNA by PEMF in human osteoblast-like cell line designated MG-63, wherein there were increases in TGF-β1, collagen, and osteocalcin synthesis. EMF stimulated an increase in TGF-β1 in both hypertrophic and atrophic cells from human non-union tissue. Further studies demonstrated an increase in both TGF-β1 mRNA and protein in osteoblast cultures resulting from a direct effect of EMF on a calcium/calmodulin-dependent pathway. Cartilage cell studies have shown similar increases in TGF-β1 mRNA and protein synthesis from EMF, demonstrating a therapeutic application to joint repair. U.S. Pat. No. 4,315,503 (1982) to Ryaby, U.S. Pat. No. 7,468,264 (2008) to Brighton and U.S. Pat. No. 5,723,001 (1998) and U.S. Pat. No. 7,744,524 (2010) to Pilla typify the research conducted in this field.

However, prior art in this field has not produced electromagnetic signals configured specifically to accelerate the asymmetrical kinetics of the binding of intracellular ions to their associated buffers which regulate the biochemical signaling pathways living systems employ for growth, repair and maintenance. The result is that application of prior art devices, such as BGS devices and PRF devices, requires excessively long treatment times with associated prolonged patient morbidity, equivocal outcomes, and unnecessarily higher health care expenses.

Therefore, a need exists for an apparatus and a method that more effectively modulates the biochemical pathways that regulate tissue growth, repair and maintenance by configuring EMF signals specifically to accelerate the asymmetrical kinetics of ion binding to intracellular buffers which regulate the biochemical signaling pathways living systems employ for growth, repair and maintenance. A method based upon the current invention will be more effective by shortening treatment times, producing enhanced outcomes, reducing morbidity and reducing the cost of health care. An apparatus based upon the current invention incorporates miniaturized circuitry and light weight coil applicators or electrodes thus allowing the apparatus to be low cost, portable and, if desired, disposable. A further need exists for an apparatus and method that incorporates the asymmetrical kinetics of ion binding to intracellular buffers to configure electromagnetic waveforms to increase the rate of ion binding and enhance the biochemical signaling pathways living systems employ for growth, repair and maintenance. This shortens treatment times, produces enhanced outcomes, reduces morbidity and the cost of health care, and incorporates miniaturized circuitry and light weight applicators that can be constructed to be implantable.

SUMMARY OF THE DISCLOSURE

An apparatus and a method for delivering electromagnetic signals configured specifically to accelerate the asymmetrical kinetics of the binding of intracellular ions to their respective intracellular buffers, to enhance the biochemical signaling pathways plant animal and human molecules, cells, tissues, organs, portions of entire organisms and entire organisms employ for growth, repair and maintenance. A preferred embodiment according to the present invention utilizes a repetitive burst of arbitrary non-thermal waveforms configured to maximize the bound concentration of intracellular ions at their associated molecular buffers to enhance the biochemical signaling pathways living systems employ for growth, repair and maintenance. Non-thermal electromagnetic waveforms are selected first by choosing the ion and the intracellular buffer, for example $Ca^{2+}$ and CaM, among the many ion-buffer combinations within the living cell, which determines the frequency range within which the signal must have non-thermal frequency components of sufficient, but non-thermal and non-destructive, amplitude to accelerate the kinetics of ion binding. Signals comprise a pulse duration, random signal duration or carrier period which is less than half of the ion bound time to increase the voltage in the target pathway so as to maximally accelerate ion binding to maximally modulate biochemical signaling pathways to enhance specific cellular and tissue responses to physical and chemical perturbations.

In preferred embodiments of the present invention, signals comprise bursts of at least one of sinusoidal, rectangular, chaotic or random wave shapes; have burst duration less than about 100 msec, with frequency content less than about 100 MHz, repeating at less than about 1000 bursts per second. Peak signal amplitude in the ion-buffer binding pathway is less than about 1000 V/m. One preferred embodiment according to the present invention comprises about a 10 to about a 50 millisecond burst of radio frequency sinusoidal waves in the range of about 1 to about 100 MHz, incorporating radio frequencies in the industrial, scientific and medical (hereinafter known as ISM) band, for example 27.12 MHz, but it may be 6.78 MHz, 13.56 MHz or 40.68 MHz in the short wave frequency band, repeating between about 0.1 and about 10 bursts/sec. Such waveforms can be delivered via inductive coupling with a coil applicator or via capacitive coupling with electrodes in electrochemical contact with the conductive outer surface of the target.

It is an object of the present invention to configure a waveform which accelerates the kinetics of $Ca^{2+}$ binding to CaM, consisting of about a 1 to about a 10 msec burst of between about 5 MHz to about 50 MHz in the ISM band, repeating between about 1 and about 10 bursts/sec and inducing a peak electric field between about 1 and about 100 V/m, then coupling the configured waveform using a generating device such as ultra-lightweight wire or printed circuit coils that are powered by a waveform configuration device such as miniaturized electronic circuitry.

It is another object of the present invention to configure a waveform which accelerates the kinetics of $Ca^{2+}$ binding to CaM, consisting of about a 1 to about a 10 msec burst of 27.12 MHz radio frequency sinusoidal waves, repeating between about 1 and about 5 bursts/sec and inducing a peak electric field between about 1 and about 100 V/m, then coupling the configured waveform using a generating device such as ultra-lightweight wire, printed circuit coils or conductive garments that are powered by a waveform configuration device such as miniaturized electronic circuitry which is programmed to apply the aforementioned waveform at fixed or variable intervals, for example for 1 minute every 10 minutes, or for 10 minutes every hour, or for any other regimen found to be beneficial for a prescribed treatment.

It is another object of the present invention to apply electromagnetic waveforms to plants, animals and humans which accelerate the asymmetrical kinetics of the binding of intracellular ions to their associated intracellular buffers, by configuring the waveforms to contain repetitive frequency components of sufficient amplitude to increase the bound concentration of the intracellular ion to its associated intracellular buffer, thereby to enhance the biochemical signaling pathways of molecules, cells, tissues, organs, portions of entire organisms and entire organisms employ for growth, repair and maintenance.

It is yet another object of the present invention to apply electromagnetic waveforms to plants, animals and humans which match the asymmetrical kinetics of the binding of $Ca^{2+}$ to CaM by configuring the waveforms to contain repetitive frequency components of sufficient amplitude to accelerate and increase the binding of $Ca^{2+}$ to CaM, thereby enhancing the CaM-dependent nitric oxide (NO)/cyclic guanosine monophosphate (cGMP) signaling pathway.

Another object of the present invention is to configure electromagnetic waveforms to contain repetitive frequency components of sufficient amplitude to accelerate and increase the binding of $Ca^{2+}$ to CaM, thereby enhancing the CaM-dependent NO/cGMP signaling pathway to accelerate blood and lymph vessel dilation for relief of post-operative and post traumatic pain and edema.

Another object of the present invention is to configure electromagnetic waveforms to contain repetitive frequency components of sufficient amplitude to accelerate and increase the binding of $Ca^{2+}$ to CaM, thereby enhancing the CaM-dependent NO/cGMP signaling pathway, or any other signaling pathway, to enhance angiogenesis and microvascularization for hard and soft tissue repair.

Another object of the present invention is to configure electromagnetic waveforms to contain repetitive frequency components of sufficient amplitude to accelerate and increase the binding of $Ca^{2+}$ to CaM, thereby enhancing the CaM-dependent NO/cGMP signaling pathway, or any other signaling pathway, to enhance bone repair.

It is another object of the present invention to configure electromagnetic waveforms to contain repetitive frequency components of sufficient amplitude to accelerate and increase the binding of $Ca^{2+}$ to CaM, thereby enhancing the CaM-dependent NO/cGMP signaling pathway, or any other signaling pathway to enhance cartilage repair.

It is another object of the present invention to configure electromagnetic waveforms to contain repetitive frequency components of sufficient amplitude to accelerate and increase the binding of $Ca^{2+}$ to CaM, thereby enhancing the CaM-dependent NO/cGMP signaling pathway, or any other signaling pathway, to reverse or prevent osteoporosis.

It is another object of the present invention to configure electromagnetic waveforms to contain repetitive frequency components of sufficient amplitude to accelerate and increase the binding of $Ca^{2+}$ to CaM, thereby enhancing the CaM-dependent NO/cGMP signaling pathway, or any other signaling pathway, to accelerate deoxyribonucleic acid (hereinafter known as DNA) synthesis by living cells.

It is yet another object of the present invention to configure electromagnetic waveforms to contain repetitive frequency components of sufficient amplitude to accelerate and increase the binding of $Ca^{2+}$ to CaM, thereby enhancing the CaM-dependent NO/cGMP signaling pathway to modulate growth factor release, such as basic fibroblast growth factor (bFGF), vascular endothelial growth factor (VGEF), bone morphogenic protein (BMP), or any other growth factor production by living cells.

Another object of the present invention is to configure electromagnetic waveforms to contain repetitive frequency components of sufficient amplitude to accelerate and increase the binding of $Ca^{2+}$ to CaM, thereby enhancing the CaM-dependent NO/cGMP signaling pathway, or any other signaling pathway, to modulate cytokine, such as interleukin 1-beta (IL-1β), interleukin-6 (IL-6), or any other cytokine production by living cells.

Another object of the present invention is to configure electromagnetic waveforms to contain repetitive frequency components of sufficient amplitude to accelerate and increase the binding of $Ca^{2+}$ to CaM, thereby enhancing the CaM-dependent NO/cGMP signaling pathway, or any other signaling pathway, to accelerate the production of matrix proteins for tissue repair and maintenance.

It is another object of the present invention to configure electromagnetic waveforms to contain repetitive frequency components of sufficient amplitude to accelerate and increase the binding of $Ca^{2+}$ to CaM, thereby enhancing the CaM-dependent NO/cyclic adenosine monophosphate (cAMP) signaling pathway, or any other signaling pathway, to modulate cell and tissue differentiation.

It is yet another object of the present invention to configure electromagnetic waveforms to contain repetitive frequency components of sufficient amplitude to accelerate and increase the binding of $Ca^{2+}$ to CaM, thereby enhancing the CaM-dependent NO/cAMP signaling pathway, or any other signaling pathway, to prevent or reverse neurodegeneration.

Another object of the present invention is to configure electromagnetic waveforms to contain frequency components of sufficient amplitude to accelerate the binding of $Ca^{2+}$ to CaM, thereby enhancing the CaM-dependent NO/cGMP signaling pathway to modulate heat shock protein release from living cells.

Another object of the present invention is to configure electromagnetic waveforms to contain frequency components of sufficient amplitude to accelerate the binding of any intracellular ion to its associated buffer in order to up regulate or down regulate the messenger ribonucleic acid (mRNA) or gene associated with any enzyme, cytokine or growth factor living tissue employs for repair, growth and maintenance.

For example, described specifically herein are electromagnetic treatment devices for accelerating cytosolic ion binding to a corresponding cytosolic buffer to modulate a biochemical signaling pathway employed for tissue growth, repair and maintenance. These devices may be configured to increase the voltage across a target ion binding pathway according to the asymmetrical binding kinetics of the target pathway, wherein the target ion binding pathway has an ion bound time. In some variations, these devices include: an applicator; and a signal generator configured to apply an electromagnetic signal to the applicator to induce, in the target pathway, a peak electric field less than about 100 V/m, wherein the signal generated by the signal generator has a pulse duration, random signal duration or carrier period which is less than twice the ion bound time, applied in a burst of waveforms having a burst duration of greater than 10 μsec and a signal repetition rate greater than 0.01 waveforms or bursts per second.

Any appropriate application may be used including a coil applicator and an electrode applicator.

The target ion binding pathway may comprise calcium binding to calmodulin, and the on bound time may be between about $10^{-2}$-10 sec.

As a consequence of the specific parameters for effectively modulating tissue as described herein, the devices may be made lightweight, portable, and/or disposable. In particular, these devices may be configured to be worn, and may be included as part of a garment, therapeutic device, anatomical support (e.g., brace), or the like. In general, these electromagnetic treatment devices may be configured to be compatible with a diagnostic or surgical device or method, and/or compatible with a pharmacological intervention or treatment.

These waveforms generated by the control circuit may have a carrier frequency within the ISM band. For example, in some variations, the waveforms generated by the control circuit have a carrier frequency of approximately 27.12 MHz.

Also described herein are methods for electromagnetic treatment of plants, animals, and humans by accelerating cytosolic ion binding to a corresponding cytosolic buffer in a target pathway to modulate a biochemical signaling pathways plants, animals and humans employ for tissue growth, repair and maintenance. In some variations, the methods include the steps of: activating an electromagnetic treatment device to treat the target pathway by inducing an electric field waveform having a pulse duration, random signal duration or carrier period which is less than twice the cytosolic ion bound time to increase the voltage in the target pathway so as to accelerate ion binding of the cytosolic ion to the buffer, thereby modulating the target pathway.

For example, the step of activating may comprise applying an electromagnetic signal to an applicator to induce, in the target pathway, a peak electric field less than about 100 V/m. The step of activating may comprise applying an electromagnetic signal to an applicator to apply a burst of waveforms having a burst duration of greater than 10 μsec and a signal repetition rate greater than 0.01 waveforms or bursts per second. Further, the step of activating comprises applying an electromagnetic signal to a coil applicator, and/or an electrode applicator.

In many of the variations described herein, the target ion binding pathway comprises calcium binding to calmodulin, and the on bound time may be between about $10^{-2}$-10 sec.

In one example, the step of activating comprises applying waveforms consisting of about 1 to about 10 msec burst of between about 5 MHz to about 50 MHz in the ISM band, repeating between about 1 and about 5 bursts/sec and inducing a peak electric field between about 1 and about 100 V/m.

In general, the step of activating may comprise applying EMF waveforms configured to modulate a particular pathway or achieve a particular desired result. For example, system may apply EMF waveforms configured to modulate the production of cytokines and growth factors that any living organism employs in response to any physical or chemical insult. Other examples include (but are not limited to): applying EMF waveforms configured to: up regulate or down regulate the mRNA or gene associated with each growth factor or cytokine any living organism employs in response to any physical or chemical insult; enhance the biochemical signaling pathways of molecules, cells, tissues, organs, portions of entire organisms and entire organisms employ for growth, repair and maintenance; modulate biochemical signaling in anti-inflammatory pathways, biochemical signaling in cytokine release pathways, biochemical signaling in growth factor release pathways; for chronic and acute musculoskeletal pain relief; edema and lymph reduction, anti-inflammatory, post-surgical and post-operative pain and edema relief, nerve, bone and organ pain relief, angina pain relief, increased local blood flow, microvascular blood perfusion, treatment of tissue and organ ischemia, cardiac tissue ischemia, brain tissue ischemia from stroke or traumatic brain injury, treatment of neurological injury and neurodegenerative diseases such as Alzheimer's and Parkinson's; wound repair, bone repair, tissue repair; osteoporosis treatment and prevention; degenerative bone disease treatment and prevention; angiogenesis, neovascularization; enhanced immune response; treatment of diabetes Types I and II; enhanced effectiveness of pharmacological agents; nerve regeneration, skeletal muscle regeneration, cardiac muscle regeneration; cancer treatment; prevention of apoptosis; modulation of heat shock proteins for prophylaxis and response to injury or pathology; modulate plasticity and cognition in humans and animals; modulate neurotransmitter release to modulate cognition and neuromuscular junction activity.

Other examples include applying EMF waveforms according to a regime defined to maximize the desired physiological outcome of tissue growth, repair and maintenance, or cognition.

In some variations the step of activating may include applying EMF waveforms configured to employ a carrier frequency within those employed by mobile communication and wireless devices.

Also described herein are methods of treating a region of a patient's body to enhance calmodulin-dependent signaling pathways, the method comprising: placing an electromagnetic treatment device on or over a region of the patient's body to be treated; activating an electromagnetic treatment device to generate an electric field having a pulse duration, random signal duration or carrier period which is less than twice the bound time of cytosolic calcium to calmodulin to accelerate calcium ion binding to calmodulin in the region of the patient's body. For example, the step of activating may comprise generating an electric field comprising an about 1 to about 10 msec burst of between about 5 MHz to about 50 MHz waves in the ISM band, repeating between about 1 and about 10 bursts/sec and inducing a peak electric field between about 1 and about 100 V/m. In some variations, the burst of waves has a carrier frequency of about 27.12 MHz.

In any of the variations described, the burst of waves comprises one of: sinusoidal, rectangular, chaotic, or random wave shapes.

An electromagnetic device may be placed on or against the patient in an appropriate position. For example, the step of placing may comprise placing a coil applicator of the electromagnetic treatment device on or over the region of the patient's body to be treated.

In general, the systems and methods described herein may be used to enhance CaM-dependent signaling, including NO/cGMP signaling, to achieve a variety of specific results, including, for example: to accelerate blood and lymph vessel dilation for relief of post-operative, post traumatic and musculoskeletal pain and edema; enhance angiogenesis and microvascularization for hard and/or soft tissue repair; enhance bone repair; enhance cartilage repair; to reverse or prevent osteoporosis; accelerate deoxyribonucleic acid synthesis; to modulate growth factor release; to modulate cytokine production; to accelerate the production of matrix proteins for tissue repair and maintenance; to modulate cell and tissue differentiation; to prevent or reverse neurodegeneration; to modulate heat shock protein release; to modulate neurotransmitter release to modulate cognition and neuromuscular junction activity; up regulate or down regulate the mRNA or gene expression associated with an enzyme, cytokine or growth factor employed for repair, growth and maintenance of tissue.

Also described herein are methods of applying a wearable electromagnetic treatment device to drive the binding of calcium to calmodulin in a target tissue by applying electromagnetic waveforms to a tissue that match the asymmetrical kinetics of binding of calcium to calmodulin, thereby enhancing calmodulin-dependent signaling, the method comprising: positioning a wearable applicator of an electromagnetic treatment device adjacent to the target tissue; and providing an electromagnetic signal to the applicator from the electromagnetic treatment device to induce an electric field of amplitude of less than about 100 V/m at the target tissue and wherein the signal comprises an about 1 to about 10 msec burst of between about 5 MHz to about 50 MHz carrier waves in the ISM band, repeating between about 1 and about 10 bursts/sec; whereby calmodulin-dependent signaling is enhanced in the target tissue.

As mentioned, the step of positioning may include placing a coil applicator of the electromagnetic treatment device on or over the region of the patient's body to be treated, which device is programmed to deliver an EMF waveform configured to enhance CaM-dependent signaling to do one or more of: accelerate blood and lymph vessel dilatation for relief of post-operative, post traumatic and musculoskeletal pain and edema; enhance angiogenesis and microvascularization for hard and/or soft tissue repair; enhance bone repair; enhance cartilage repair; reverse or prevent osteoporosis; accelerate deoxyribonucleic acid synthesis; modulate growth factor release; modulate cytokine production; modulate the production of matrix proteins for tissue repair and maintenance; modulate cell and tissue differentiation; prevent or reverse neurodegeneration; modulate heat shock protein release; up regulate or down regulate the mRNA or gene expression associated with an enzyme, cytokine or growth factor employed for repair, growth and maintenance of tissue.

In some variations, positioning comprises placing a coil applicator of the electromagnetic treatment device on or over the region of the patient's body to be treated, which device is programmed to deliver an EMF waveform configured to enhance CaM-dependent signaling for chronic and acute musculoskeletal pain relief; edema and lymph reduction, anti-inflammatory, post-surgical and post-operative pain and edema relief, nerve, bone and organ pain relief, angina pain relief, increased local blood flow, microvascular blood perfusion, treatment of tissue and organ ischemia, cardiac tissue ischemia, brain tissue ischemia from stroke or traumatic brain injury, treatment of neurological injury and neurodegenerative diseases such as Alzheimer's and Parkinson's; wound repair, bone repair, tissue repair; osteoporosis treatment and prevention; degenerative bone disease treatment and prevention; angiogenesis, neovascularization; enhanced immune response; treatment of diabetes Types I and II; enhanced effectiveness of pharmacological agents; nerve regeneration, skeletal muscle regeneration, cardiac muscle regeneration; cancer treatment; prevention of apoptosis; modulation of heat shock proteins for prophylaxis and response to injury or pathology.

In addition, in any of these methods, the step of positioning may include placing a coil applicator of the electromagnetic treatment device on or over the region of the patient's body to be treated, which device is programmed to deliver an EMF waveform configured to enhance CaM-dependent signaling to modulate plasticity and cognition in humans and animals. In some variations, positioning comprises placing a coil applicator of the electromagnetic treatment device on or over the region of the patient's body to be treated, which device is programmed to deliver an EMF waveform configured to enhance CaM-dependent signaling to modulate neurotransmitter release to modulate cognition and neuromuscular junction activity.

The above and yet other objects and advantages of the present invention will become apparent from the hereinafter set forth Brief Description of the Drawings and Detailed Description.

BRIEF DESCRIPTION OF THE DRAWINGS

Preferred embodiments and applications of the present invention will be described below in more detail, with reference to the accompanying drawings.

DETAILED DESCRIPTION

Figure 1:
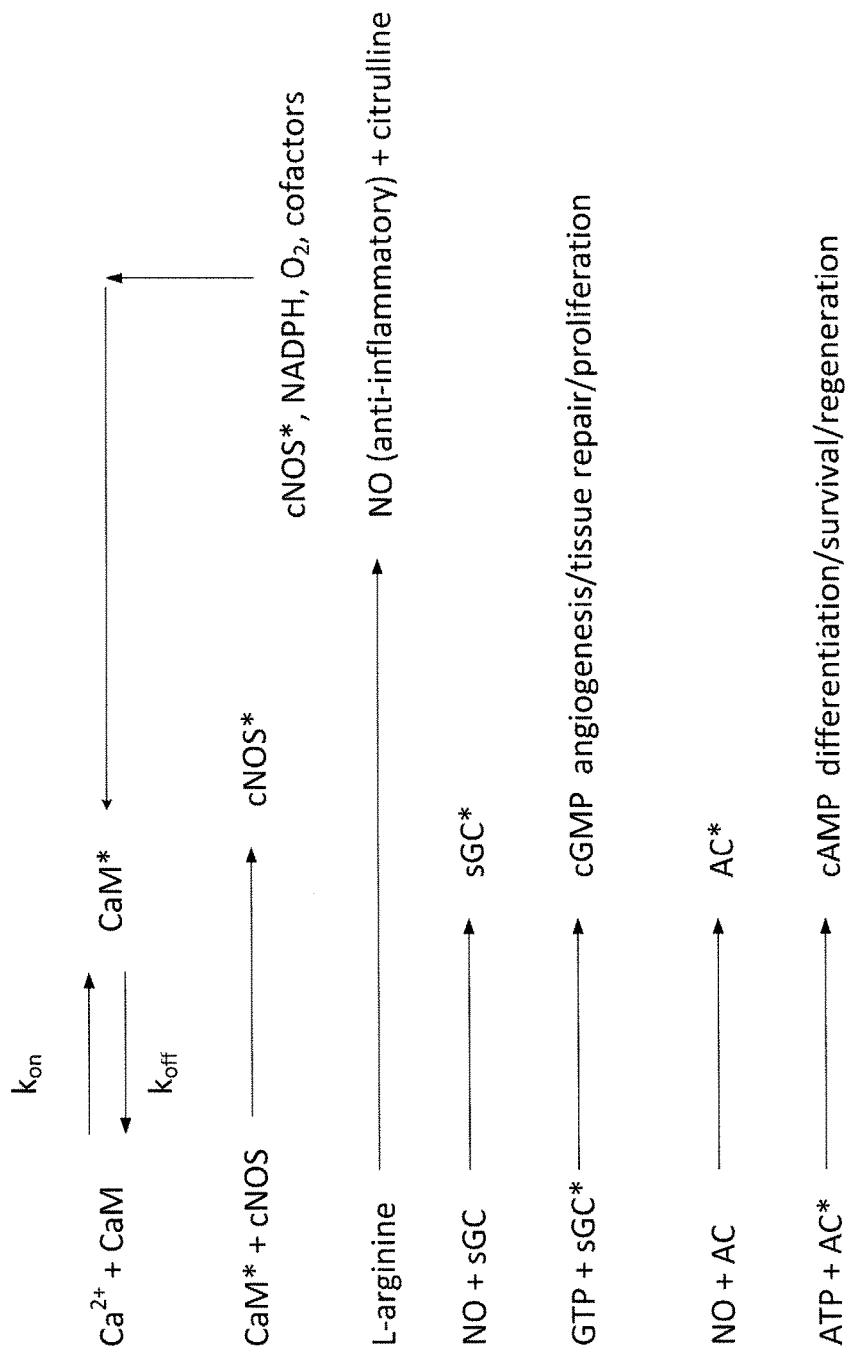
FIG. 1 is a schematic representation of the biological EMF transduction pathway which is a representative target pathway of EMF signals configured as embodiments of the present invention. According to the present invention, an EMF signal can be configured to accelerate cytosolic ion binding to a cytosolic buffer, such as $Ca^{2+}$ binding to CaM, because the rate constant for binding, $k_{on}$ is voltage-dependent and $k_{on}$ is much greater than the rate constant for unbinding, $k_{off}$, imparting rectifier-like properties to ion-buffer binding, such as $Ca^{2+}$ binding to CaM; cNOS* represents activated constitutive nitric oxide synthase (cNOS), catalyzes the production of NO from L-arginine; sGC* is activated guanylyl cyclase which catalyzes cyclic guanosine monophosphate (cGMP) formation when NO signaling modulates the tissue repair pathway; AC* is activated adenylyl cyclase, which catalyzes cyclic adenosine monophosphate (cAMP) when NO signaling modulates differentiation and survival.

Basal levels of intracellular $Ca^{2+}$ are typically 50-100 nM, tightly maintained by a number of physiological calcium buffers. It is generally accepted that transient elevations in cytosolic $Ca^{2+}$ from external stimuli as simple as changes in temperature and mechanical forces, or as complex as mechanical disruption of tissue, rapidly activate CaM, which equally rapidly activates the cNOS enzymes, i.e., endothelial and neuronal NOS, or eNOS and nNOS, respectively. Studies have shown that both isoforms are inactive at basal intracellular levels of $Ca^{2+}$, however, their activity increases with elevated $Ca^{2+}$, reaching half-maximal activity at about 300 nM. Thus, nNOS and eNOS are regulated by changes in intracellular $Ca^{2+}$ concentrations within the physiological range. In contrast, a third, inducible isoform of NOS (iNOS), which is up regulated during inflammation by macrophages and/or neutrophils, contains CaM that is tightly bound, even at low resting levels of cytosolic $Ca^{2+}$, and is not sensitive to intracellular $Ca^{2+}$.

Once cNOS is activated by CaM it converts its substrate, L-arginine, to citrulline, releasing one molecule of NO. As a gaseous free radical with a half-life of about 5 sec, NO diffuses locally through membranes and organelles and acts on molecular targets at a distance up to about 200 μm. The low transient concentrations of NO from cNOS can activate soluble guanylyl cyclase (sGC), which catalyzes the synthesis of cyclic guanosine monophosphate (cGMP). The CaM/NO/cGMP signaling pathway is a rapid response cascade which can modulate peripheral and cardiac blood flow in response to normal physiologic demands, as well as to inflammation. This same pathway also modulates the release of cytokines, such as interleukin-1beta (IL-1β) and growth factors such as basic fibroblast growth factor (FGF-2) and vascular endothelial growth factor (VEGF) which have pleiotropic effects on cells involved in tissue repair and maintenance.

Following an injury, e.g., a bone fracture, torn rotator cuff, sprain, strain or surgical incision, repair commences with an inflammatory stage during which the pro-inflammatory cytokine IL-1β is rapidly released. This, in turn, up-regulates iNOS, resulting in the production of large amounts of NO in the wound bed. Continued exposure to NO leads to the induction of cyclooxygenase-2 and increased synthesis of prostaglandins which also play a role in the inflammatory phase. While this process is a natural component of healing, when protracted, it can lead to increased pain and delayed or abnormal healing. In contrast, CaM/eNOS/NO signaling has been shown to attenuate levels of IL-1β and down-regulate iNOS. As tissue further responds to injury, the CaM/NO/cGMP cascade is activated in endothelial cells to stimulate angiogenesis, without which new tissue growth cannot be sustained. Evidence that non-thermal EMF can modulate this cascade is provided by several studies. An early study showed that the original BGS signal promoted the creation of tubular, vessel-like, structures from endothelial cells in culture in the presence of growth factors. Another study using the same BGS signal confirmed a seven-fold increase in endothelial cell tubularization in vitro. Quantification of angiogenic proteins demonstrated a five-fold increase in FGF-2, suggesting that the same BGS signal stimulates angiogenesis by increasing FGF-2 production. This same study also reported increased vascular in-growth more than two-fold when applied to an implanted Matrigel plug in mice, with a concomitant increase in FGF-2, similar to that observed in vitro. The BGS signal significantly increased neovascularization and wound repair in normal mice, and particularly in diabetic mice, through an endogenous increase in FGF-2, which could be eliminated by using a FGF-2 inhibitor. Similarly, a pulse modulated radio frequency (PRF) signal of the type used clinically for wound repair was reported to significantly accelerate vascular sprouting from an arterial loop transferred from the hind limb to the groin in a rat model. This study was extended to examine free flap survival on the newly produced vascular bed. Results showed 95% survival of PRF-treated flaps compared to 11% survival in the sham-treated flaps, suggesting a significant clinical application for PRF signals in reconstructive surgery.

The proposed EMF transduction pathway relevant to tissue maintenance, repair and regeneration, begins with voltage-dependent $Ca^{2+}$ binding to CaM, which is favored when cytosolic $Ca^{2+}$ homeostasis is disrupted by chemical and/or physical insults at the cellular level. Ca/CaM binding produces activated CaM which binds to, and activates, cNOS, which catalyzes the synthesis of the signaling molecule NO from L-arginine. This pathway is shown in its simplest schematic form in FIG. 1. According to the present invention, EMF can accelerate the kinetics of $Ca^{2+}$ binding to CaM, the first step of a well characterized cascade that responds to chemical or physical insults. Ca/CaM binding is kinetically asymmetrical, i.e., the rate of binding exceeds the rate of dissociation by several orders of magnitude ($k_{on} \gg k_{off}$), driving the reaction in the forward direction. Ca/CaM binding has been well characterized, with the binding time constant reported to be in the range of $10^{-2}$-$10^{-3}$ sec. In contrast, release of $Ca^{2+}$ from CaM cannot occur until cNOS* has converted L-arginine to citrulline and NO, which takes the better part of a second. Subsequent reactions involving NO depend upon the cell/tissue state. For example, tissue repair requires a temporal sequence of inflammatory, anti-inflammatory, angiogenic and proliferative components. Endothelial cells orchestrate the production of FGF-2 and VEGF for angiogenesis. For each of these phases, early NO production by endothelial cells, leading to increased cGMP by these, as well as other NO targets, such as vascular smooth muscle, would be expected to be modulated by an EMF effect on sGC via Ca/CaM binding. In contrast, nerve or bone regeneration may require other pathways leading to differentiation during development and growth, and prevention of apoptosis, as in response to injury or neurodegenerative diseases. For these cases, early cyclic adenosine monophosphate (cAMP) formation would be modulated by an EMF effect on sAC via Ca/CaM binding.

The substantial asymmetry of Ca/CaM binding kinetics provides a unique opportunity to configure EMF signals that selectively modulate $k_{on}$. In general, if $k_{on} \gg k_{off}$, and $k_{on}$ is voltage-dependent, according to the present invention, ion binding could be increased with an exogenous electric field signal having a carrier period or pulse duration that is significantly shorter than the mean lifetime of the bound ion. This applies to the CaM signaling pathway, causing it to exhibit rectifier-like properties, i.e., to yield a net increase in the population of bound $Ca^{2+}$ because the forward (binding) reaction is favored.

The change in surface concentration, $\Delta\Gamma$, of $Ca^{2+}$ at CaM is equal to the net increase in the number of ions that exit the outer Helmholtz plane, penetrate the water dipole layer at the aqueous interface of the binding site, and become bound in the inner Helmoltz plane. For the general case of ion binding, evaluation of Ca/CaM binding impedance, ZA(s), allows calculation of the efficacy of any given waveform in that pathway by evaluating the frequency range over which the forward binding reaction can be accelerated. Thus, binding current, IA(t), is proportional to the change in surface charge (bound ion concentration) via dq(t)/dt, or, in the frequency domain, via sqA(s). IA(s) is, thus, given by:

$$I_A(s) = sq_A(s) = s\Gamma_o f(\Delta\Gamma(s)) \quad (1)$$

where s is the real-valued frequency variable of the Laplace transform. Taking the first term of the Taylor expansion of equation 1 gives:

$$I_A(s) = q_\Gamma s \Gamma_o \Delta\Gamma(s) \quad (2)$$

where $q_\Gamma = \partial q/\partial \Gamma$, a coefficient representing the dependence of surface charge on bound ion concentration. $\Delta\Gamma(s)$ is a function of the applied voltage waveform, E(s), and, referring to the reaction scheme in FIG. 1, of the change in concentration of eNOS*, defined as $\Delta\Phi(s)$:

$$\Delta\Gamma(s) = k_{on}/\Gamma_o s[-\Delta\Gamma(s) + aE(s) + \Delta\Phi(s)] \quad (3)$$

where $\Gamma_o$ is the initial surface concentration of Ca2+(homeostasis), and $a = \partial\Gamma/\partial E$, representing the voltage dependence of Ca2+ binding. Referring to the reaction scheme in FIG. 1, it may also be seen that eNOS* depends only upon Ca2+ binding, i.e., $\Delta\Gamma(s)$. Thus:

$$\Delta\Phi(s) = \upsilon_\Phi/\Phi_o s[-\Delta\Phi(s) - \Delta\Gamma(s)] \quad (4)$$

where $\upsilon\Phi$ is the rate constant for Ca/CaM binding to eNOS and $\Phi_o$ is the initial concentration of eNOS* (homeostasis).

Using equations 2, 3 and 4, and for $k_{on} \gg \upsilon_\Phi$, ZA(s) may be written:

$$Z_A(s) = \frac{E(s)}{I_A(s)} = \frac{1}{q_\Gamma a}\left[\frac{1 + \Gamma_o/k_{on}}{\Gamma_o s}\right] \quad (5)$$

Equation 5 describes the overall frequency response of the first binding step in a multistep ion binding process at an electrified interface, wherein the second step requires that the bound ion remain bound for a period of time significantly longer than the initial binding step. For this case, the first ion binding step is represented by an equivalent electrical impedance which is functionally equivalent to that of a series $R_A$-$C_A$ electric circuit, embedded in the overall dielectric properties of the target. $R_A$ is inversely proportional to the binding rate constant ($k_{on}$), and $C_A$ is directly proportional to bound ion concentration.

The present invention teaches that an electromagnetic field, for which pulse duration or carrier period is less than about half of the bound ion lifetime can be configured to maximize current flow into the capacitance $C_A$, which will increase the voltage, $E_b(s)$, where s is the LaPlace frequency, across $C_A$. $E_b(s)$ is a measure of the increase in the surface concentration of the binding ion in the binding sites of the buffer, above that which occurs naturally in response to a given physiological state. The result is an increase in the rate of biochemical signaling in plant, animal and human repair, growth and maintenance pathways which results in the acceleration of the normal physiological response to chemical or physical stimuli. The following equation demonstrates the relation between the configured electromagnetic waveform, E(s) and $E_b(s)$.

$$E_b(s) = \frac{(1/sC_A)E(s)}{(R_A^2 + (1/sC_A)^2)^{1/2}} \quad (6)$$

The present invention further teaches that a time-varying electromagnetic field for which pulse duration or carrier period is less than about half of the bound ion lifetime of $Ca^{2+}$ binding to CaM will maximize the current flow into the Ca/CaM binding pathway to accelerate the CaM-dependent signaling which plants, animals and humans utilize for tissue growth, repair and maintenance. In particular, a time-varying electromagnetic field may be configured to modulate CaM-dependent NO/cGMP signaling which accelerates; pain and edema relief, angiogenesis, hard and soft tissue repair, repair of ischemic tissue, prevention and repair of neurodegenerative diseases, nerve repair and regeneration, skeletal and cardiac muscle repair and regeneration, relief of muscle pain, relief of nerve pain, relief of angina, relief of degenerative joint disease pain, healing of degenerative joint disease, immunological response to disease, including cancer.

A preferred embodiment according to the present invention is an electromagnetic signal which accelerates the kinetics of $Ca^{2+}$ binding by maximizing non-thermal $E_b(s)$ at its CaM binding sites, consisting of a 1-10 msec pulse burst of 27.12 MHz radio frequency sinusoidal waves, repeating between about 1 and about 5 bursts/sec and inducing a peak electric field between about 1 and about 100 V/m, then coupling the configured waveform using a generating device such as ultra lightweight wire coils that are powered by a waveform configuration device such as miniaturized electronic circuitry which is programmed to apply the waveform at fixed or variable intervals, for example 1 minute every 10 minutes, 10 minutes every hour, or any other regimen found to be beneficial for a prescribed treatment.

Referring to FIG. 1, examples of the biochemical signaling pathways which can be modulated by acceleration of $Ca^{2+}$ binding to CaM with non-thermal electromagnetic fields (EMF) configured according to the present invention are illustrated. The application of non-thermal EMF, configured according to the present invention, instantaneously accelerates the kinetics of $Ca^{2+}$ binding to CaM, the first step of a well characterized signaling cascade which a plant, animal or human organism utilizes to respond to chemical or physical insults. Ca/CaM binding is kinetically asymmetrical, i.e., the rate of binding exceeds the rate of dissociation by several orders of magnitude ($k_{on} \gg k_{off}$), therefore the application of EMF will instantaneously drive the reaction in the forward direction. The Ca/CaM binding time constant is in the range of 1 to 10 milliseconds. In contrast, the release of $Ca^{2+}$ from CaM cannot occur until cNOS* has converted L-arginine to citrulline and NO, which takes the better part of a second. Subsequent reactions involving NO depend upon the cell/tissue state. For example, tissue repair requires a temporal sequence of inflammatory, anti-inflammatory, angiogenic and proliferative components. Endothelial cells orchestrate the production of FGF-2 and VEGF for angiogenesis. For each of these phases, early NO production by endothelial cells, leading to increased cGMP by these, as well as other NO targets, such as vascular smooth muscle, are modulated by an EMF effect on GC via Ca/CaM binding. In contrast, nerve or bone regeneration require other pathways leading to differentiation during development and growth, and prevention of apoptosis, as in response to injury or neurodegenerative diseases. For these cases, early cAMP formation is modulated by an EMF effect on AC via Ca/CaM binding.

Figure 2:
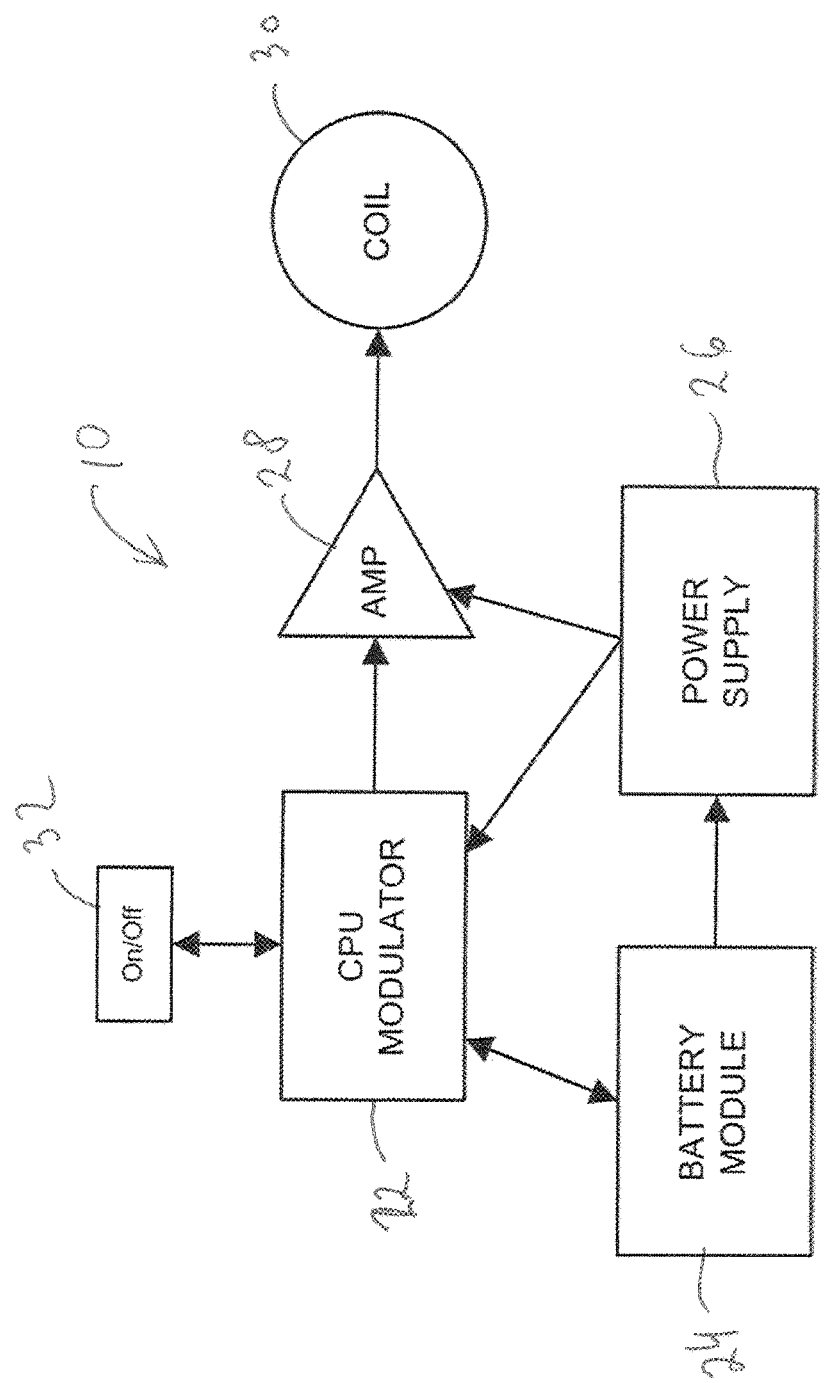
FIG. 2 is a block diagram of miniaturized circuitry for use with a coil applicator according to a preferred embodiment of the present invention, wherein a CPU modulator, a preferred embodiment of which is an 8 bit 4 MHz microcontroller, but other bit-MHz combination micro-controllers may be used, is programmed, according to the present invention to deliver an EMF waveform to the target ion binding pathway, such as that illustrated in FIG. 4, via a coil applicator, or via electrodes (not shown). A BATTERY, which may be rechargeable, operated device with an ON/OFF switch, a POWER SUPPLY and output amplifier, AMP, is illustrated.

FIG. 2 illustrates a preferred embodiment of an apparatus according to the present invention. A CPU MODULATOR 22, a preferred embodiment of which is an 8 bit 4 MHz micro-controller, but other bit-MHz combination micro-controllers may be used, is programmed, according to the present invention, for a given carrier frequency or pulse duration, for example about 27.12 MHz sinusoidal wave; a given burst duration, for example about 3 msec; to provide a given in situ peak electric field, for example 20 V/m; a given treatment time, for example about 15 min.; and a given treatment regimen, for example about 10 min. every about hour. The BATTERY MODULE 24, in a preferred embodiment, has an output voltage of 3.3 V, but other voltages can be used, supplies DC voltage and current to a POWER SUPPLY 26 which provides operating power to the CPU MODULATOR 22 and the output amplifier 28, hereinafter referred to as AMP 28. The electromagnetic signal is applied inductively to the plant animal or human target with a COIL applicator 30, or capacitively with electrodes in electrochemical contact with the out conductive surface of the target structure (not shown). The COIL applicator is flexible and circular, but may also be anatomically conformable, such as oval or saddle shaped, with a diameter of between about 2 cm to about 50 cm. An electromagnetic treatment, or, if desired, an electromagnetic treatment regimen, is initiated with the ON/OFF switch 32, which may be mechanical or electronic.

Figure 3:
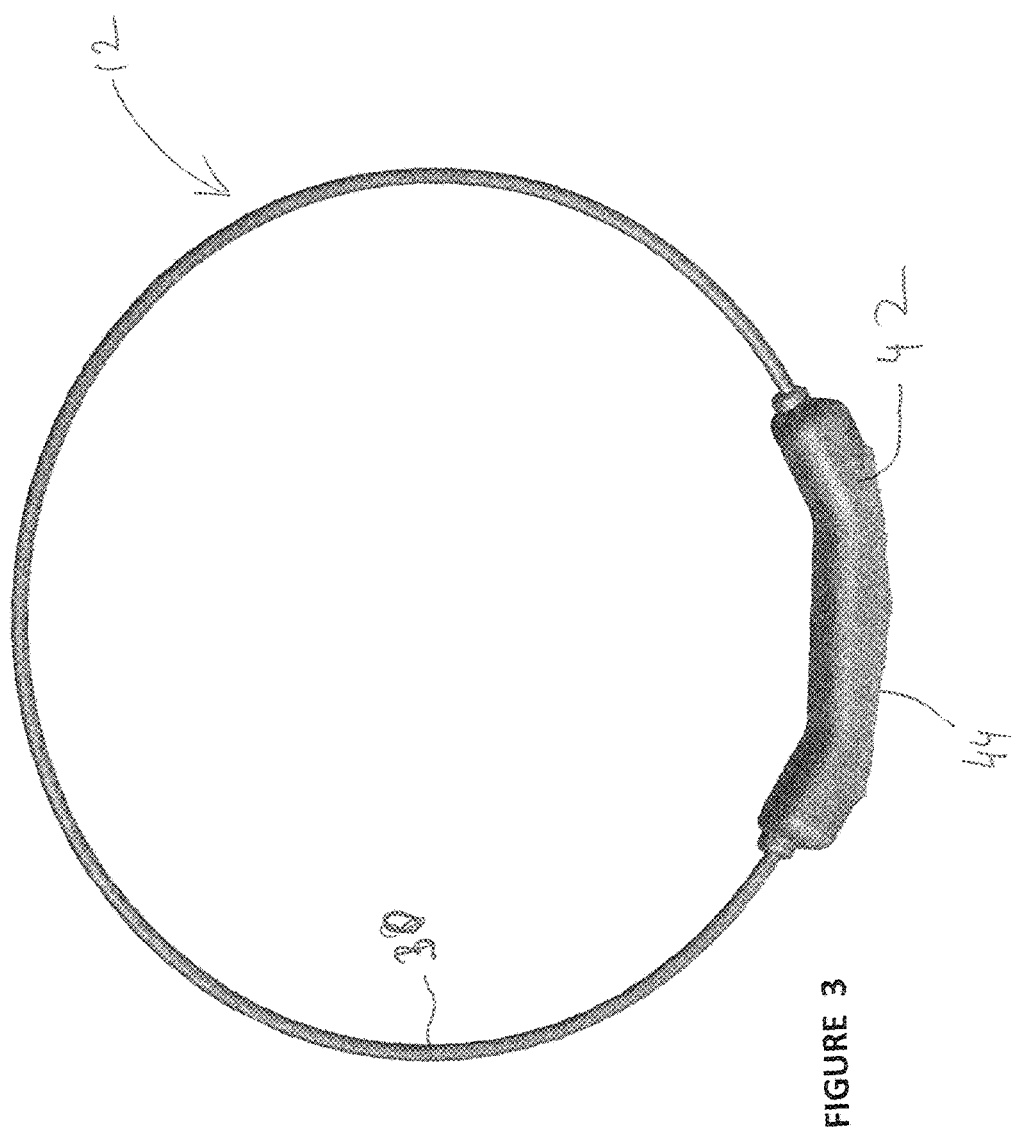
FIG. 3 is drawing of a portable and disposable coil/generator combination according to a preferred embodiment of the present invention. The coil applicator is flexible and circular, but may be conformable, for example oval or saddle shaped. The miniature signal generator, a block diagram of which is illustrated in FIG. 2, is an integral portion of the coil applicator. The EMF device illustrated in FIG. 3 is portable, and, if desired, disposable, and can be used alone or incorporated into an anatomical positioning device such as a dressing, bandage, compression bandage, compression dressing; knee, elbow, lower back, shoulder, foot, and other body portion wrap and support; garments, footwear, gloves, and fashion accessories; mattress pads, seat cushions, furniture, beds; in seats or beds within cars, motorcycles, bicycles, buses, trains, planes, boats and ships.

A preferred embodiment according to the present invention combines signal generation and coil 30 or electrode applicator 42 in one portable or disposable unit 12 such as illustrated in FIG. 3 for the case of an inductively coupled signal. When electrical coils 30 are used as the applicator, the electrical coils 30 can be powered with a time varying magnetic field that induces a time varying electric field in a target pathway structure according to Faraday's law. An electromagnetic signal generated by a circuit 10 such as shown in FIG. 2 can also be applied using electrochemical coupling, wherein electrodes 44 are in direct contact with skin or another outer electrochemically conductive boundary of a target pathway structure. In yet another embodiment according to the present invention, the electromagnetic signal generated by the generating circuit of FIG. 2 can also be applied using electrostatic coupling wherein an air gap exists between a generating device such as an electrode 44 and a target pathway structure such as a molecule, cell, tissue, or organ of a plant, animal or human for which any therapeutic or prophylactic effect is desired. An advantageous result of application of the preferred embodiment according to the present invention is that a living orgnism's wellbeing can be maintained and enhanced.

The inductive device 12 illustrated in FIG. 3 is flexible, portable and, if desired, disposable; and can be used alone or incorporated into an anatomical positioning device such as a dressing, bandage, compression bandage, compression dressing; knee, elbow, lower back, shoulder, foot, and other body portion wrap and support; garments, footwear, gloves, and fashion accessories; mattress pads, seat cushions, furniture, beds; in seats or beds within cars, motorcycles, bicycles, buses, trains, planes, boats and ships.

Figure 4:
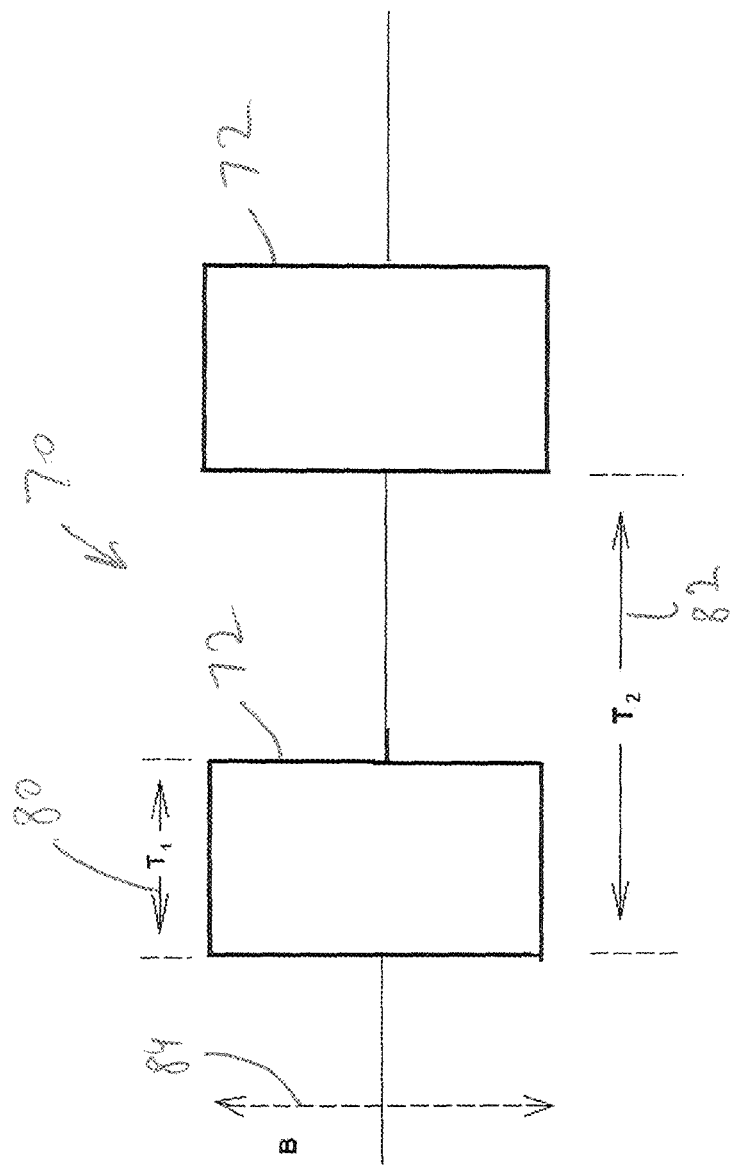
FIG. 4 depicts a waveform delivered to a target pathway structure of a plant, animal or human, such as a molecule, cell, tissue, organ, partial or entire organism, according to a preferred embodiment of the present invention. Burst duration and period are represented by $T_1$ and $T_2$, respectively. It is noted that the signal within the rectangular box designated as $T_1$ can be rectangular, sinusoidal, chaotic or random, provided the waveform duration or carrier period is less than one-half of the target ion bound time. The peak induced electric field is related to the peak induced magnetic field, designated as B in this figure, via Faraday's Law of Induction.

Referring to FIG. 4, an embodiment according to the present invention of an induced electric field waveform 70 delivered to a target pathway structure of a plant, animal or human, such as a molecule, cell, tissue, organ, partial or entire organism is illustrated. Burst duration 80 and period 82 are represented by $T_1$ and $T_2$, respectively. A burst of duration $T_1$ between about 1 msec and about 20 msec, containing a repetitive rectangular pulse 72, a sinusoidal wave or a chaotic or random waveform (not shown), having, respectively, a period $T_2$ or frequency less than half of the bound time of the target ion binding pathway, repeats between about 1 and about 10 bursts/sec, and induces a peak electric field 84 of 20 V/m which is proportional to a peak applied time varying magnetic field B 84 of 50 mG according to Faraday's Law of Induction. The induced electric field illustrated in FIG. 3 is configured according to the teaching of the present invention to modulate biochemical signaling pathways in plant, animal and human targets, such as those illustrated in FIG. 1.

EXAMPLE 1

The biochemical signaling pathways illustrated in FIG. 1 show that the effect of EMF, configured according to embodiments of the present invention, on the synthesis of NO from eNOS, by increasing the rate of $Ca^{2+}$ binding to CaM, will increase the rate of angiogenesis, which increases the rate of tissue repair. Angiogenesis requires the production of basic fibroblast growth factor (bFGF) and vascular endothelial growth factor (VEGF), which first require that eNOS be activated by CaM, as illustrated in FIG. 1, to synthesize NO by endothelial cells.

Figure 5:
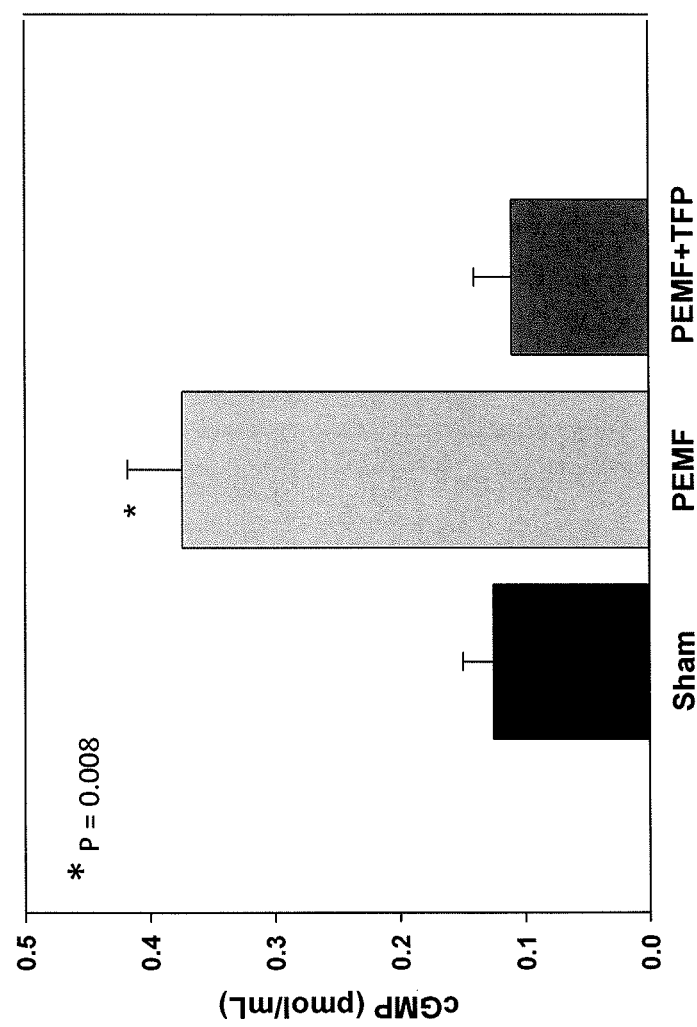
FIG. 5 Effect of a waveform configured according to an embodiment of the present invention on human umbilical vascular endothelial cell (HUVEC) cultures. 15 min exposure to a signal consisting of a 3 msec burst of a 27.12 MHz carrier, repeating at 2 bursts/sec, and with a peak induced electric field of 40 V/m produced more than a 3-fold increase in cGMP. Use of a CaM antagonist, trifluoperazine, (TFP) abolished the EMF effect, providing evidence that $Ca^{2+}$ binding was accelerated by an EMF signal configured according to an embodiment of the present invention in endothelial cells.

This study examined the effect of EMF, configured according to an embodiment of the current invention, on the CaM/NO/cGMP pathway to modulate cGMP production from human umbilical vascular endothelial cells (HUVECs) in culture. HUVEC cells in serum-free medium were removed from the incubator 15 min prior to EMF exposure. The temperature change from 37° C. to approximately 25° C. was a repeatable "injury" designed to increase intracellular $Ca^{2+}$. Cultures were then exposed at room temperature for 15 min to EMF within the central portion of a single-turn 20 cm diameter coil (antenna). The EMF signal consisted of a 3 msec burst of 27.12 MHz sinusoidal waves repeating at 2 bursts/sec. The average induced electric field was 32±6 V/m. Cultures remained at room temperature for an additional 15 min after EMF exposure, after which cells were lysed for cGMP analysis with enzyme-linked immunosorbent assay (ELISA). In some cultures trifluoroperazine (TFP) a CaM antagonist was employed to test whether increased Ca/CaM binding via EMF led to the observed increased levels of cGMP. The results, summarized in FIG. 5, demonstrate that a single 15-minute exposure to an EMF signal, configured according to the present invention, produced nearly a 3-fold increase in cGMP, and that this EMF effect was abolished by TFP.

Figure 6:
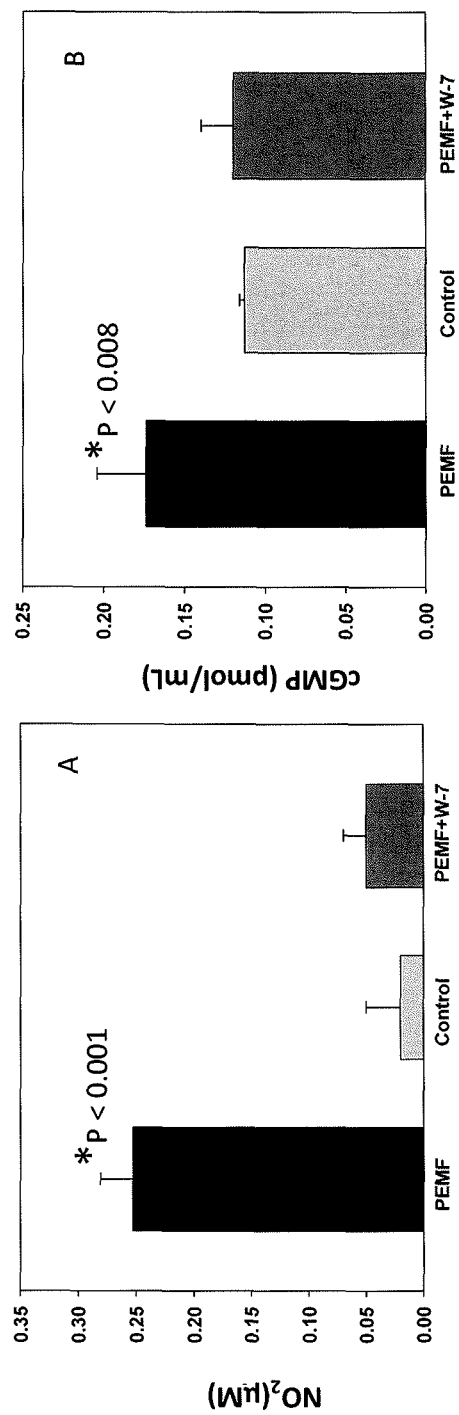
FIG. 6 Effect of a waveform configured according to an embodiment of the present invention on nitric oxide (NO) release from MN9D neuronal cell cultures. Cells were incubated to serum-free medium in presence or absence of the CaM antagonist, W-7. After 30 min exposure to a waveform, consisting of a 3 msec burst of a 27.12 MHz carrier, repeating at 2 bursts/sec, at 20 V/m peak induced electric field, NO was quantified in conditioned medium (Griess reaction) EMF increased NO several-fold over that from control cultures, which was blocked by W-7 (A, FIG. 6); cells were lysed and cGMP evaluated with ELISA. Results showed cGMP was increased significantly by EMF, which could be blocked by W-7 (B, FIG. 6). Both results are illustrated in FIGS. 6A and 6B, and indicate signals configured according to the present invention can modulate CaM-dependent signaling in neurons.
Figure 7:
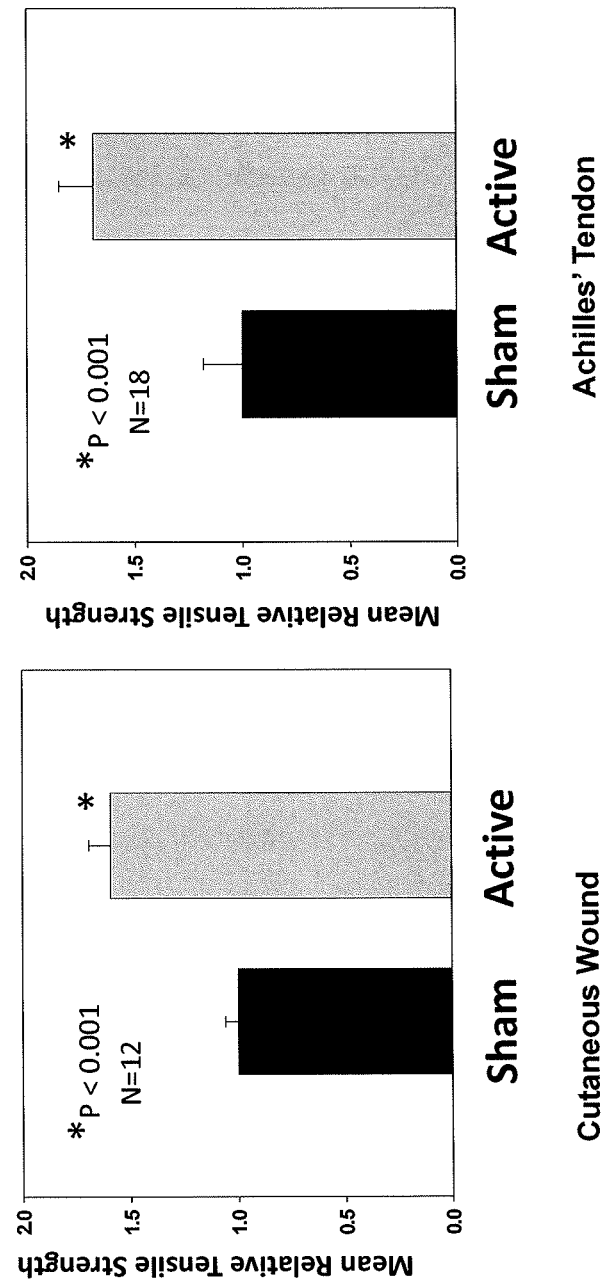
FIG. 7 Effect of an EMF signal, configured according to an embodiment of the present invention, consisting of a 2 msec burst of a 27.12 MHz sinusoidal wave at 20 V/m, on cutaneous full thickness wound (Left) and transected Achilles' tendon (Right) healing in the rat. The results show tensile strength of the treated wound and tendon is respectively 59% and 69% stronger at 21 days as a result of twice daily EMF treatment for 30 minutes.

These results provide mechanistic support for the reported acceleration of cutaneous wound repair by 59% and Achilles' tendon repair by 69% at 21 days in rat models as measured by tensile strength, and illustrated in FIG. 6, in randomized, blinded studies using an EMF signal identical to that employed for HUVEC cultures, as above. This study also provided additional mechanistic support for a randomized blinded animal study in which exposure for 20 min twice daily to the EMF waveform used in the HUVEC study significantly increased angiogenesis in vivo (+150%, P<0.001) 7 days following a thermal myocardial injury in the rat, as illustrated in FIG. 7. CD-31 antibody was employed to identify newly formed blood vessels in tissue sections throughout the penumbra surrounding the ischemic core of the cardiac lesion. The PRF effect was eliminated in rats that received L-nitrosoarginine methyl ester (L-NAME), a non-selective cNOS inhibitor, in the drinking water. The conclusion is that the EMF signal, configured according to the present invention, modulated angiogenesis through CaM-dependent NO/cGMP signaling in the cutaneous wound and cardiac ischemia animal models.

EXAMPLE 2

According to an application of the present invention an EMF signal, configured according to an embodiment of the present invention to modulate CaM-dependent signaling, similar to that employed for HUVEC cultures of Example 1, and applied for 30 minutes to the MN9D dopaminergic neuronal cell line, increased NO production by several-fold in a serum depletion paradigm and produced a 45% increase in cGMP. The EMF effects on NO and cGMP were inhibited by the CaM antagonist N-(6-Aminohexyl)-5-chloro-1-naphthalenesulfonamide hydrochloride (W-7), indicating the EMF signal acted in this neuronal culture according to the transduction mechanism illustrated in FIG. 1. These results are summarized in FIG. 6. The effect of the same EMF signal on cAMP production in MN9D cells was also studied. MN9D cells in serum free medium were removed from the incubator (repeatable temperature stress injury to transiently increase intracellular $Ca^{2+}$) and exposed to EMF for 15 min. cAMP was evaluated in cell lysates by ELISA. Results demonstrate that an EMF signal, configured according to an embodiment of the present invention, increased cAMP production by several-fold. Notably, the c-NOS inhibitor L-NAME abolished the PEMF effect on cAMP. The results, summarized in FIG. 7, indicate EMF signals, configured according to an embodiment of the present invention, are also able to affect neuronal differentiation and survival.

EXAMPLE 3

An EMF signal, configured according to an embodiment of the present invention was applied to an in vivo wound repair model. A rat wound model has been well characterized both biomechanically and biochemically, and was used in this study. Healthy, young adult male Sprague Dawley rats weighing more than 300 grams were utilized. The animals were anesthetized with an intraperitoneal dose of Ketamine 75 mg/kg and Medetomidine 0.5 mg/kg. After adequate anesthesia had been achieved, the dorsum was shaved, prepped with a dilute betadine/alcohol solution, and draped using sterile technique. Using a #10 scalpel, an 8-cm linear incision was performed through the skin down to the fascia on the dorsum of each rat. The wound edges were bluntly dissected to break any remaining dermal fibers, leaving an open wound approximately 4 cm in diameter. Hemostasis was obtained with applied pressure to avoid any damage to the skin edges. The skin edges were then closed with a 4-0 Ethilon running suture. Post-operatively, the animals received Buprenorphine 0.1-0.5 mg/kg, intraperitoneal. They were placed in individual cages and received food and water ad libitum.

EMF exposure was non-thermal pulse modulated radio frequency configured according to an embodiment of the present invention. For this signal burst duration was 2000 μsec and the amplitude and repetition rate were 0.05G and 2 bursts/sec, respectively. EMF was applied for 30 minutes twice daily. Tensile strength was performed immediately after wound excision. Two 1 cm width strips of skin were transected perpendicular to the scar from each sample and used to measure the tensile strength in $kg/mm^2$. The strips were excised from the same area in each rat to assure consistency of measurement. The strips were then mounted on a tensiometer. The strips were loaded at 10 mm/min and the maximum force generated before the wound pulled apart was recorded. The final tensile strength for comparison was determined by taking the average of the maximum load in kilograms per $mm^2$ of the two strips from the same wound.

The results, illustrated in FIG. 7, Left, demonstrate that an embodiment of the present invention significantly accelerated wound repair in this animal model, with application to wound repair in humans.

This example also included an experiment to test the effect of an embodiment of this invention on the rate of healing of a transected Achilles' tendon in a rat model. The Achilles tendon of male adult Sprague Dawley rats was transected and stabilized with a single suture. There was no additional mechanical stabilization. Animals were divided into sham exposed and active groups. Active animals were treated in individual plastic cages with an EMF signal configured as an embodiment of the present invention with a peak amplitude of 0.05 G. Sham exposed animals were treated identically. PEMF exposure was 30 min twice daily until sacrifice at 21 days. The tensile strength of the isolated tendon was determined using a standard laboratory tensiometer. Pull rate was 0.45 mm/sec. Treated tendons had 69% higher tensile strength than sham treated (P<0.001). The results are summarized in FIG. 7, Right.

EXAMPLE 4

Figure 8:
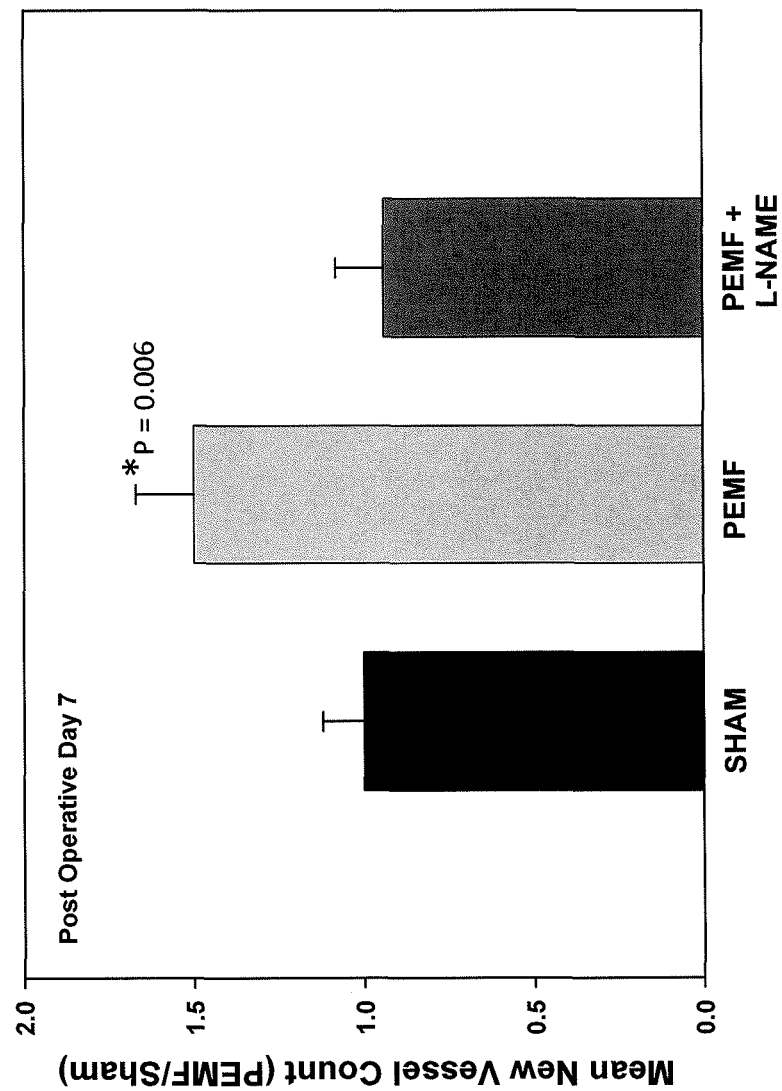
FIG. 8 Effect of an electromagnetic signal, configured according to an embodiment of the present invention consisting of a 2 msec burst of a 27.12 MHz sinusoidal wave at 20 V/m, repeating at 2 bursts/sec, on angiogenesis in a thermal myocardial necrosis model in the rat. EMF increases angiogenesis by 60% at 7 days. L-NAME, a general cNOS inhibitor fed to rats in the drinking water, eliminated the PEMF effect on angiogenesis, indicating that an EMF signal, configured as an embodiment of the present invention, accelerates $Ca^{2+}$ binding to CaM in the NO signaling cascade that regulates angiogenesis.

In this example a highly reproducible thermal myocardial injury was created in the region of the distal aspect of the Left Anterior Descending Artery at the base of the heart of adult male Sprague Dawley rats. The EMF waveform, configured as an embodiment of the present invention, was a 2 msec burst of 27.12 MHz sinusoidal waves repeating at 5 bursts/sec delivering 0.05 G at the tissue target. Five freely roaming animals in a standard rat plastic cage, with all metal portions removed, were placed within a single turn 14×21 inch coil. Exposure was 30 min twice daily for three weeks. Sham animals were identically exposed, but received no EMF signal. Upon sacrifice, myocardial tissue specimens were stained with CD-31 to evaluate the presence of newly forming blood vessels and capillaries in peri-ischemic tissue. Results at 21 days showed that number of vessels and capillaries in peri-ischemic myocardial tissue was increased by approximately 100% (p<0.001) in EMF vs sham exposed animals. That an EMF signal, configured as an embodiment of the present invention, modulated CaM-dependent NO release, as illustrated in FIG. 1, was verified by feeding animals L-NAME, a cNOS inhibitor, in their drinking water for 7 days. EMF, configured as an embodiment of the present invention, accelerated angiogenesis at 7 days by 60%. The EMF effect was abolished by L-NAME. This result is illustrated in FIG. 8.

EXAMPLE 5

Figure 9:
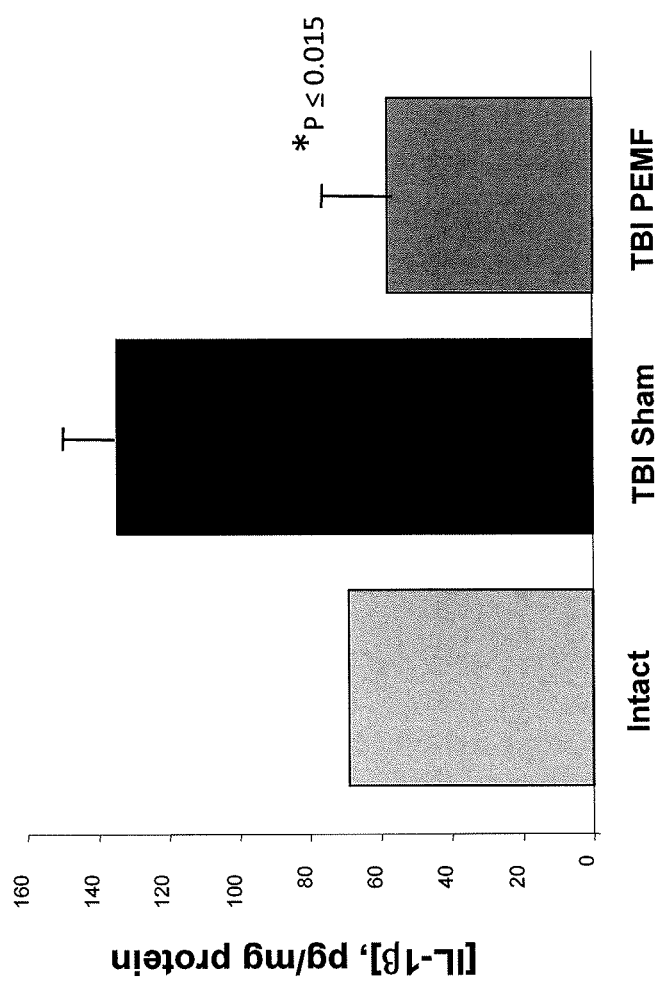
FIG. 9 Groups of rats were subjected to contusive traumatic brain injury (TBI) and treated with an EMF signal configured according to an embodiment of the present invention. Treated animals received a 3 msec burst of 27.12 MHz sinusoidal carrier waves, repeating at 2 bursts/sec and delivering 20V/m peak induced electric field to the target tissue according to a 5 min every 20 min exposure regimen for 6 hours. Control animals received no signal. Brains were collected at 6 hours and IL-1β levels were measured. The results, illustrated in FIG. 9 show that IL-1β levels in control group brains increased rapidly after the onset of TBI, but were maintained at normal levels in the EMF group. Net EMF effect on IL-1β was more than 2-fold at 6 hours, closely following the EMF effect on IL-1β in the clinical study described in FIG. 10. These results show that an EMF signal, configured according to an embodiment of the present invention can rapidly prevent early tissue damage from TBI.

In this example, groups of rats were subjected to contusive traumatic brain injury (TBI) and treated with an EMF signal configured as an embodiment of the present invention. 300-350 g Sprague-Dawley were anesthetized with ketamine (75 mg/kg) and medetomidine (0.5 mg/kg). When anesthetic depth was reached, the scalp was reflected and a metal disk measuring 10 mm in diameter and 2 mm thickness was secured with epoxy symmetrically onto the skull at the midline equally between lambda and bregma, two anatomical landmarks defined by the intersections of the coronal and lambdoid sutures with the mid-sagittal suture, respectively, to minimize the risk of skull fracture upon impact. The animal was then secured to a firm (spring constant=4) foam pad. Injury was produced using a "weight-drop" type impact device, consisting of a clear plastic cylinder with internal diameter of 1-inch and a weight that fits just within the cylinder. After impact, the scalp was approximated using interrupted nylon sutures and anesthesia was reversed by 1 mg/kg atipamezole. This injury induces inflammation, edema, and neuronal death without a secondary impact (bounce) or deleterious side effects (skull fracture, death). Active animals were treated with an EMF signal configured as an embodiment of the present invention, applied in a 5 min on in every 20 min regimen for 6 hours. Animals were sacrificed and brains homogenized to determine the EMF effect on the master pro-inflammatory cytokine, IL-1β. The results, illustrated in FIG. 9, show that EMF reduced IL-1β by approximately 2-fold in treated vs control animals. This result indicates that EMF, configured according to an embodiment of the present invention, produced a very rapid drop in the inflammatory response to traumatic brain and cervical injury which no other pharmacological or physical modality has been able to achieve. An important factor is that these results were obtained with a portable disposable device which can be incorporated in kits for field response to brain trauma, stroke and other neurological injuries.

EXAMPLE 6

Figure 10:
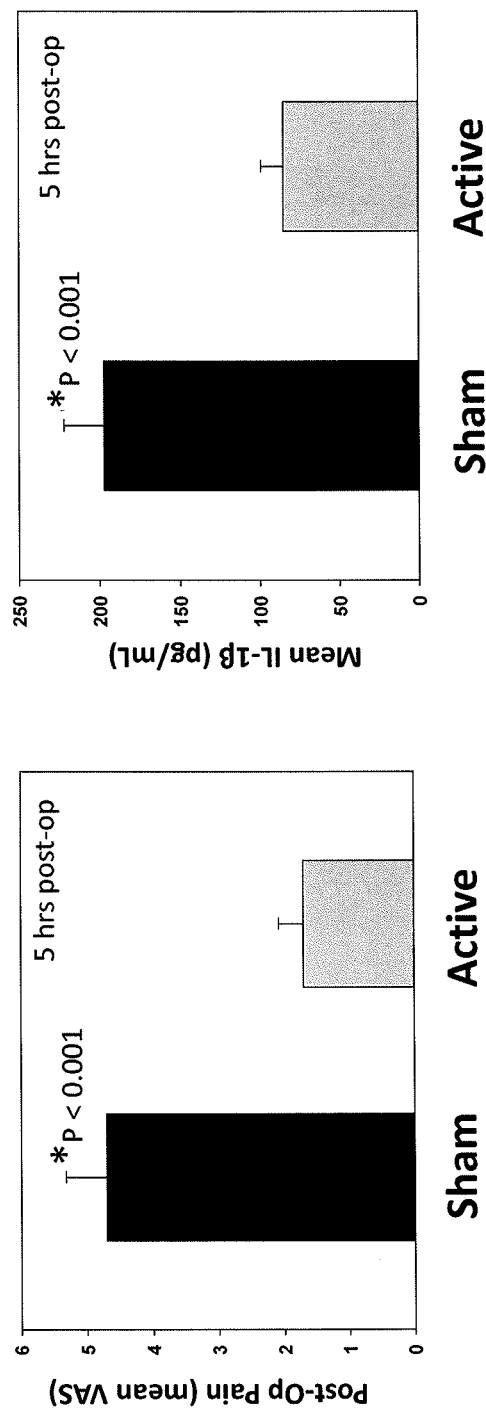
FIG. 10 Effect of a radio frequency PEMF signal configured according to an embodiment of the present invention in a randomized double-blind clinical study on breast reduction patients. Post-operative pain was approximately 2.5-fold lower in the active cohorts by 5 hrs post-op. A measure of the inflammatory cytokine, IL-1β in wound exudates showed nearly the same 2.5 fold decrease in the active cohort over the same time range, indicating that a signal configured according to the present invention modulates CaM-dependent NO/cGMP signaling which is known to down-regulate IL-1β, thereby accelerating the reduction of the master pro-inflammatory cytokine IL-1β via the signaling pathway schematized in FIG. 1.

In this example the effect of a pulse modulated radio frequency EMF signal, configured according to an embodiment of the present invention, on post-operative pain was studied in a randomized double-blind clinical study on breast reduction patients. Patients were treated with EMF, configured according to an embodiment of the present invention, delivered to the target tissue with a disposable device, similar to that illustrated in FIG. 3, which was incorporated in the post surgical dressing. Treatment regimen for active patients was 30 min every 4 hours for three days. Sham patients received the same EMF device which did not deliver a signal. Wound exudates were collected and pain was assessed by participants using a validated Visual Analog Scale (VAS). Concentrations of IL-1β, a major pro-inflammatory cytokine, were approximately 3-fold lower at 5 hours post-op (P<0.001) in wound exudates from EMF-treated patients compared to those of the control group. EMF also produced a concomitant 2-fold decrease in pain at 1 hour (P<0.01) and a 2.5-fold decrease at 5 hours post-op (P<0.001), persisting to 48 hours post-op. No significant changes in VAS scores were observed in the control group. Furthermore, the increased levels of analgesia were reflected in a 2.2-fold reduction in narcotic use in patients receiving active treatment over the first 24 hours post-op (P=0.002). Importantly, the time course for both pain and IL-1β reduction were concomitant, showing that EMF, configured to modulate CaM/NO signaling in an embodiment according to the present invention, produced endogenous changes in the dynamics of IL-1β availability, which impacts the many known subsequent inflammatory events that are mediated by this cytokine, including those leading to post-operative pain. These results, which are illustrated in FIG. 10, demonstrate that EMF, configured according to an embodiment of the present invention produced a rapid, non-pharmacological, non-invasive post-operative anti-inflammatory response which significantly reduced patient morbidity and the cost of health care, and enhanced healing.

EXAMPLE 7

Figure 11:
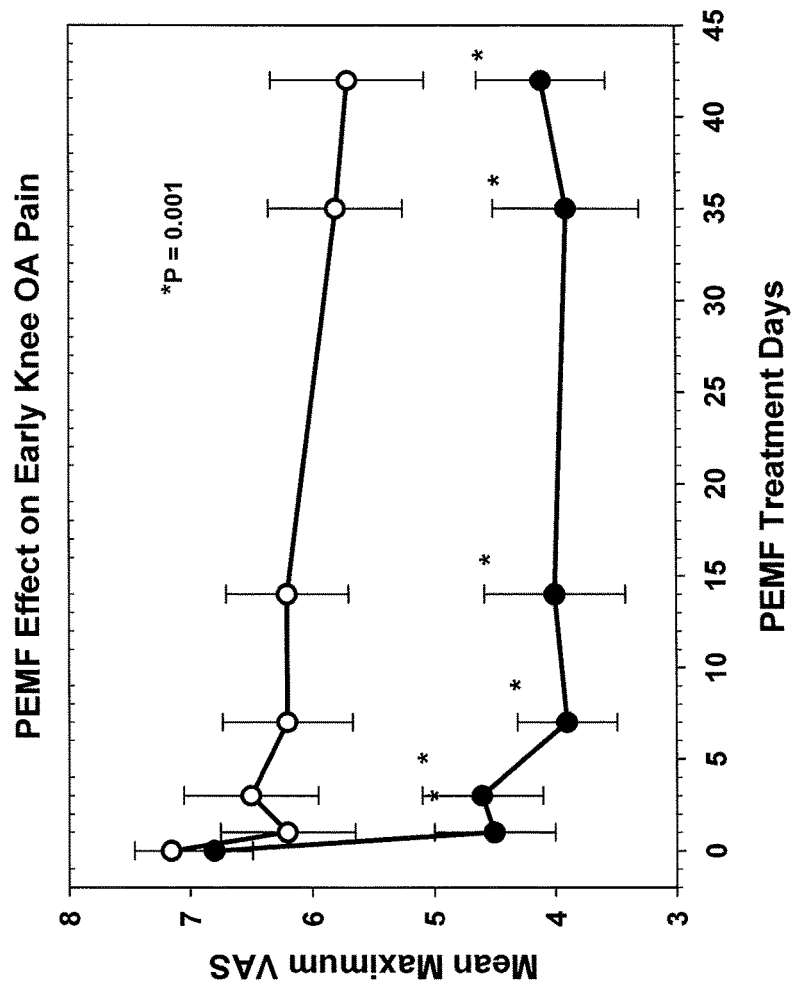
FIG. 11 Effect of a radio frequency EMF signal, configured according to the present invention, to modulate CaM/NO signaling, on pain from knee osteoarthritis in a randomized double-blind clinical study. Mean maximum pain (VAS) in the active cohort decreased by 2-fold compared with its baseline value within the first 24 hours, which persisted to day 42. There was no significant decrease in pain in the sham cohort at any time point.

In this example, a randomized double-blind clinical study, which employed an EMF signal configured according to an embodiment of the present invention, produced a rapid decrease in pain from osteoarthritis (OA) of the knee. A total of 37 patients (19 active, 18 sham) entered the study. The EMF signal consisted of a 7 msec burst of 6.8 MHz sinusoidal waves repeating at 1/sec with 0.05 G peak amplitude, used for 15 minutes twice daily, or as needed for pain relief. Maximum VAS scores were obtained at baseline (day 0) and daily for the first 14 days and from day 29 to day 42. Results show that EMF caused an approximate 2-fold decrease in mean VAS with respect to baseline by the end of day 1 in the treated group, which persisted to day 42 (P<0.001). There was no significant decrease in mean maximum pain scores at any time point in the sham group. The results, illustrated in FIG. 11 show that pain from knee OA was very rapidly reduced and was maintained at a reduced level for 42 days, indicating OA progression was slowed or stopped.

CaM-dependent NO production rapidly mediates relief of pain from knee OA by increasing circulation, decreasing nerve irritation, and decreasing inflammation. This is similar to the kinetics of the rapid reduction of pain in the breast reduction study of Example 6, wherein EMF, configured as an embodiment of the present invention, also produced a rapid initial reduction in pain within 5 hours post-op. This shows that the mechanisms of action are similar in both studies. EMF activates the CaM/cNOS pathway producing an initial rapid and transient release of NO leading to vaso- and lymphatic dilation. This causes a rapid reduction of effusion (edema) with a concomitant rapid reduction of pain. This means the mechanism of the EMF effect involves the down-regulation of IL-1β with its consequent attenuation of inflammation in this patient population.

Having described embodiments and examples applications for an apparatus and a method for delivering electromagnetic treatment which accelerates cytosolic ion binding to respective cytosolic buffers, thereby modulating signaling cascades which humans, animals and plants utilize for growth, repair and maintenance, it is noted that modifications and variations can be made by persons skilled in the art in light of the above teachings. It is therefore to be understood that changes may be made in the particular embodiments of the invention disclosed which are within the scope and spirit of the invention.

What is claimed is:

1. A method for electromagnetic treatment of plants, animals, and humans by accelerating ion binding to a corresponding molecule in a target pathway, the target pathway operating at a voltage, to modulate activity of biochemical signaling pathways plants, animals and humans employ for tissue growth, repair and maintenance, the method comprising:
    activating an electromagnetic treatment device to treat the target pathway by inducing an electric field waveform having a pulse duration, random signal duration or carrier period which is less than twice an ion bound time to increase the voltage in the target pathway so as to accelerate ion binding of the ion to the corresponding molecule thereby modulating the target pathway,
    wherein the step of activating comprises applying an electromagnetic signal to a capacitively coupled electrode applicator.

2. A method for electromagnetic treatment of plants, animals, and humans by accelerating ion binding to a corresponding molecule in a target pathway, the target pathway operating at a voltage, to modulate activity of biochemical signaling pathways plants, animals and humans employ for tissue growth, repair and maintenance, the method comprising:
    activating an electromagnetic treatment device to treat the target pathway by applying an electromagnetic signal to a capacitively coupled electrode applicator thereby inducing an electric field waveform having a pulse duration, random signal duration or carrier period which is less than twice an ion bound time to increase the voltage in the target pathway so as to accelerate ion binding of the ion to the corresponding molecule thereby modulating the target pathway,
    wherein the step of activating comprises applying an electromagnetic signal to a electrochemically coupled electrode applicator.

3. A method of treating a region of a patient's body to enhance calmodulin-dependent signaling pathways, the method comprising:
    placing an electromagnetic treatment device on or over a region of the patient's body to be treated;
    activating the electromagnetic treatment device to generate an electric field by applying an electromagnetic signal to a capacitively coupled electrode applicator having a pulse duration, random signal duration or carrier period which is less than twice a bound time of cytosolic calcium to calmodulin to accelerate calcium ion binding to calmodulin in the region of the patient's body.

4. The method of claim 3, wherein the activating step further comprises generating an electric field comprising a 1 to 10 msec burst of a carrier frequency between 5 MHz to 50 MHz including the ISM band repeating between 1 and 10 bursts/sec and inducing a peak electric field less than 100 V/m.

5. The method of claim 4, wherein the burst of carrier frequency further comprises one of: sinusoidal, rectangular, chaotic, or random wave shapes.

6. The method of claim 3, wherein the placing step further comprises placing a coil applicator, electrode applicator, or coil and electrode applicator of the electromagnetic treatment device on or over the region of the patient's body to be treated.

7. The method of claim 3, further comprising generating an electric field having a pulse duration, random signal duration or carrier period to enhance CaM-dependent signaling, including NO/cGMP signaling to accelerate blood and lymph vessel dilation for relief of post-operative, post traumatic and musculoskeletal pain and edema.

8. The method of claim 3, further comprising generating an electric field having a pulse duration, random signal duration or carrier period to enhance CaM-dependent signaling, including NO/cGMP signaling to enhance angiogenesis and microvascularization for hard, soft or hard and soft tissue repair.

9. The method of claim 3, further comprising generating an electric field having a pulse duration, random signal duration or carrier period to enhance CaM-dependent signaling, including NO/cGMP signaling to enhance bone repair.

10. The method of claim 3, further comprising generating an electric field having a pulse duration, random signal duration or carrier period to enhance CaM-dependent signaling, including NO/cGMP signaling to enhance cartilage repair.

11. The method of claim 3, further comprising generating an electric field having a pulse duration, random signal duration or carrier period to enhance CaM-dependent signaling, including NO/cGMP signaling to reverse or prevent osteoporosis.

12. The method of claim 3, further comprising generating an electric field having a pulse duration, random signal duration or carrier period to enhance CaM-dependent signaling, including NO/cGMP signaling to accelerate deoxyribonucleic acid synthesis.

13. The method of claim 3, further comprising generating an electric field having a pulse duration, random signal duration or carrier period to enhance CaM-dependent signaling, including NO/cGMP signaling to modulate growth factor release.

14. The method of claim 3, further comprising generating an electric field having a pulse duration, random signal duration or carrier period to enhance CaM-dependent signaling, including NO/cGMP signaling to modulate cytokine production.

15. The method of claim 3, further comprising generating an electric field having a pulse duration, random signal duration or carrier period to enhance CaM-dependent signaling, including NO/cGMP signaling to accelerate the production of matrix proteins for tissue repair and maintenance.

16. The method of claim 3, further comprising generating an electric field having a pulse duration, random signal duration or carrier period to enhance CaM-dependent signaling, including NO/cGMP signaling to modulate cell and tissue differentiation.

17. The method of claim 3, further comprising generating an electric field having a pulse duration, random signal duration or carrier period to enhance CaM-dependent signaling pathways to prevent or reverse neurodegeneration.

18. The method of claim 3, further comprising generating an electric field having a pulse duration, random signal duration or carrier period to enhance CaM-dependent signaling to modulate heat shock protein release.

19. The method of claim 3, further comprising generating an electric field having a pulse duration, random signal duration or carrier period to enhance CaM-dependent signaling to modulate cognition and neuromuscular junction activity.

20. The method of claim 3, further comprising generating an electric field having a pulse duration, random signal duration or carrier period to enhance CaM-dependent signaling to up regulate or down regulate messenger ribonucleic acid or gene expression associated with an enzyme, cytokine or growth factor employed for repair, growth and maintenance of tissue.

21. A method of treating a region of a patient's body to enhance calmodulin-dependent signaling pathways, the method comprising:

placing an electromagnetic treatment device on or over a region of the patient's body to be treated;

activating the electromagnetic treatment device to generate an electric field by applying an electromagnetic signal to a capacitvely coupled electrode applicator having a pulse duration, random signal duration or carrier period which is less than a bound time of cytosolic calcium to calmodulin to accelerate calcium ion binding to calmodulin in the region of the patient's body.

22. A method of applying a wearable electromagnetic treatment device to modulate the binding of calcium to calmodulin in a target tissue by applying electromagnetic waveforms to a tissue that match asymmetrical kinetic of binding of calcium to calmodulin, thereby enhancing calmodulin-dependent signaling, the method comprising:

positioning a wearable applicator of an electromagnetic treatment device adjacent to the target tissue; and providing an electromagnetic signal to the applicator from the electromagnetic treatment device by applying an electrochemically coupled electrode applicator to induce an electric field of amplitude of less than about V/m at the target tissue and wherein the signal comprises a 1 to 10 msec burst of between 5 MHz and 50 MHz carrier waves including the ISM band, repeating at between 1 and 10 bursts/sec;

whereby calmodulin-dependent signaling is enhanced in the target tissue.

* * * * *